United States Patent
Ozawa

(10) Patent No.: US 6,879,339 B2
(45) Date of Patent: Apr. 12, 2005

(54) ELECTRONIC ENDOSCOPE SYSTEM WITH COLOR-BALANCE ALTERATION PROCESS

(75) Inventor: Ryo Ozawa, Saitama (JP)

(73) Assignee: PENTAX Corporation, Tokyo (JP)

( * ) Notice: Subject to any disclaimer, the term of this patent is extended or adjusted under 35 U.S.C. 154(b) by 330 days.

(21) Appl. No.: 10/274,998

(22) Filed: Oct. 22, 2002

(65) Prior Publication Data

US 2003/0076412 A1 Apr. 24, 2003

(30) Foreign Application Priority Data

Oct. 23, 2001 (JP) .................................... P2001-324697

(51) Int. Cl.[7] .............................................. H04N 7/18
(52) U.S. Cl. ...................................................... 348/71
(58) Field of Search ............................. 348/45, 65–72; 600/101, 109, 113; H04N 7/18

(56) References Cited

U.S. PATENT DOCUMENTS

| | | | | |
|---|---|---|---|---|
| 4,780,762 A | * | 10/1988 | Nagasaki ..................... | 348/45 |
| 4,831,437 A | * | 5/1989 | Nishioka et al. .............. | 348/71 |
| 4,870,487 A | * | 9/1989 | Noguchi ...................... | 348/70 |
| 5,398,056 A | * | 3/1995 | Yabe et al. ................... | 348/68 |
| 5,864,361 A | | 1/1999 | Sekiya et al. | |
| 5,929,899 A | | 7/1999 | Takahashi et al. | |
| 6,025,873 A | * | 2/2000 | Nishioka et al. .............. | 348/72 |
| 6,371,908 B1 | | 4/2002 | Furusawa et al. | |
| 2003/0009083 A1 | * | 1/2003 | Takahashi .................... | 600/109 |

FOREIGN PATENT DOCUMENTS

JP          200125025          1/2001

OTHER PUBLICATIONS

English Language Translation for JP Appln. No. 2001–25025.

* cited by examiner

*Primary Examiner*—Richard Lee
(74) *Attorney, Agent, or Firm*—Greenblum & Bernstein, P.L.C.

(57) ABSTRACT

An electronic endoscope system with a color-balance alteration system includes a video scope having a CCD image sensor for producing a frame of color image-pixel-signals composed of frames of red, green, and blue image-pixel-signals. In the color-balance alteration system, nine red signals are extracted from the frame of red image-pixel-signals, and the nine signals form a 3×3 matrix including a central signal, and the eight circumferential signals. All four sets of three signals are selected from the nine signals, and each set of three signals is composed of the central signal, and two neighbouring signals aligned with each other such that the central signal lies therebetween. When a signal level of the central signal is smaller than both signal levels of the two circumferential signals with respect to even one set of three signals, the signal level of signal is decreased.

6 Claims, 13 Drawing Sheets

FIG. 4

| $R_{(i-1)(j-1)}$ | $R_{(i-1)j}$ | $R_{(i-1)(j+1)}$ |
|---|---|---|
| $R_{i(j-1)}$ | $R_{ij}$ | $R_{i(j+1)}$ |
| $R_{(i+1)(j-1)}$ | $R_{(i+1)j}$ | $R_{(i+1)(j+1)}$ |

$2 \leq i \leq (m-1), 2 \leq j \leq (n-1)$

ELECTRONIC ENDOSCOPE SYSTEM WITH COLOR-BALANCE ALTERATION PROCESS

BACKGROUND OF THE INVENTION

1. Field of the Invention

The present invention relates to an electronic endoscope system in which an endoscope image is reproduced as a full color image on a TV monitor, and, in particular, to such an electronic endoscope system with a color-balance alteration process, which is constituted such that, for example, the endoscope image can be reproduced on the TV monitor as if it were sprayed with a dye-solution.

2. Description of the Related Art

As is well known, an electronic endoscope system includes a video scope that is inserted in an organ of a human body, and the video scope has a solid-state image sensor for capturing an organ image or endoscope image as a frame of image-pixel-signals. The electronic endoscope system also includes an image-signal processing unit for producing a video signal based on the frames of image-pixel-signals successively read from the solid-state image sensor, and a TV monitor for reproducing the endoscope image as a motion picture based on the video signal fed from the image-signal processing unit.

Recently, it is usual to manufacture an electronic endoscope system such that the endoscope image is reproduced as a full color motion picture on a TV monitor. Thus, a dye-spraying examination method was developed and has been used as a medical examination method in the medical field in which electronic endoscope systems are used. For example, when a subtle uneven surface of the mucous membrane of a stomach or a colon is examined, the dye-spraying medical method is utilized.

In particular, the mucous membrane surface of the stomach or the colon features a reddish orange tone as a whole, and thus it is very difficult to examine the subtle unevenness of the mucous membrane surface. In order that the subtle unevenness of the mucous membrane surface can be clearly and easily examined on a TV monitor, a bluish solution, such as an Indigo Carmine solution, is introduced into a forceps-insertion passage of the video scope, and is sprayed over the mucous membrane surface. The solution has a tendency toward gathering in fine recess areas on the mucous membrane surface, and it flows away from fine land areas on the mucous membrane surface. Namely, the fine recess areas on the mucous membrane surface are colored blue and clearly contrast with the reddish orange areas. Thus, it is possible to easily carry out an examination of the subtle unevenness of the mucous membrane surface.

However, there are various drawbacks in the dye-spraying medical examination method. For example, a dye must be harmless to a human body, and it is troublesome to develop harmless dyes. Also, the use of a dye-spraying medical examination method prolongs the medical examination time when using the electronic endoscope system, resulting in an increase in the patient's pain and discomfort. Further, once a dye-solution is sprayed, it is impossible to immediately reproduce an endoscope image without the sprayed dye-solution.

In order to resolve the above-mentioned problems, Japanese Laid-Open Patent Publication (KOKAI) No. 2001-25025 discloses an electronic endoscope system with a simulated dye-spraying process or color-balance alteration process for electronically processing an endoscope image as if it were sprayed with a blue-solution.

In particular, a full color endoscope image is formed based on three frames of three primary-color image-pixel-signals: a frame of red image-pixel-signals, a frame of green image-pixel-signals, and a frame of blue image-pixel-signals. In the color-balance alteration process, for example, nine red image-pixel-signals, forming a 3×3 matrix, are successively extracted from the frame of red image-pixel-signals, and a value of the central red image-pixel-signal is compared with an average of values of the eight surrounding circumferential red image-pixel-signals.

When the value of the central red image-pixel-signal is lower than the average of the values of the circumferential red image-pixel-signals, the central red image-pixel-signal derives from a fine recess area on a mucous membrane surface of, for example, a stomach. However, when the value of the central red image-pixel-signal is higher than the average of the values of the circumferential red image-pixel-signals, the central red image-pixel-signal derives from a fine land area on the mucous membrane surface of the stomach. The same is true for the green image-pixel-signals and the blue image-pixel-signals.

Accordingly, for example, if the frames of the three primary-color image-pixel-signals are processed such that the values of red and green image-pixel-signals, deriving from the fine recess areas, are lowered, an endoscope image can be reproduced as if it were sprayed with a bluish-solution.

In short, a fine recess area on the mucous membrane surface is detected by comparing the value of the central image-pixel-signal with the average of the eight values of the circumferential image-pixel-signals, and the values of central red and green image-pixel-signals, deriving from the fine recess area, are lowered when the fine recess area is detected.

Nevertheless, in the electronic endoscope system, as shown in the aforesaid KOKAI No. 2001-25025, there may be a case where the fine recess areas on the mucous membrane surface cannot be properly detected. For example, when the fine recess areas on the mucous membrane surface form a network of fine grooves, three aligned image-pixel-signals on the 3×3 matrix, including the central image-pixel signal, may lie on the fine groove. In this case, since the average of the eight values of the circumferential image-pixel-signals may be considerably lowered, it is not possible to properly detect the fine recess area corresponding to the central image-pixel-signal.

In another example, when a fine shallow recess area on the mucous membrane surface is adjacent to one or more fine deep recess area, and when the central image-pixel signal derives from the fine shallow recess area, the average of the eight values of the circumferential image-pixel-signals, may be considerably lowered due to the existence of the adjacent one or more fine deep recess areas. Similarly, it is not possible to properly detect the fine shallow recess area corresponding the central image-pixel-signal.

SUMMARY OF THE INVENTION

Therefore, an object of the present invention is to provide an electronic endoscope system with a color-balance alteration process, which is constituted such that the fine recess areas on mucous membrane surfaces of internal organs can be properly detected for the color-balance alteration process, so that the subtle unevenness of the mucous membrane surface can be examined.

In accordance with the present invention, an electronic endoscope system includes a video scope having a solid-state image sensor that successively produces a frame of color image-pixel-signals composed of at least two frames of different monochromatic image-pixel-signals, and comprises a color-balance alteration system for the frame of color image-pixel-signals. In the color-balance alteration system, an extraction system successively extracts a set of monochromatic image-pixel-signals from a frame of monochromatic image-pixel-signals. The set of monochromatic image-pixel-signals is composed of a central monochromatic image-pixel-signal and circumferential monochromatic image-pixel-signals surrounding the central monochromatic image-pixel-signal. A selection system selects all the sets of three monochromatic image-pixel-signals from the set of monochromatic image-pixel-signals, and each set of three monochromatic image-pixel-signals is composed of the central monochromatic image-pixel-signal and two neighbouring monochromatic image-pixel-signals aligned with each other such that the central monochromatic image-pixel-signal lies therebetween. A determination system determines whether the signal level of the central monochromatic image-pixel-signal is smaller than signal levels of the two neighbouring monochromatic image-pixel-signals for all the sets of three monochromatic image-pixel-signals. When it is determined by the determination system that the signal level of the central monochromatic image-pixel-signal is smaller than both the signal levels of the two neighbouring monochromatic image-pixel-signals with respect to only one set of the three monochromatic image-pixel-signals, a decrease system decreases the signal level of the central monochromatic image-pixel-signal.

The decrease system may comprise a subtraction system that subtracts a predetermined level value from the signal level of the central monochromatic image-pixel-signal. Alternatively, the decrease system may comprise a multiplier system that multiplies the signal level of the central monochromatic image-pixel-signal by a predetermined factor less than one.

The electronic endoscope system may comprise a first video signal production system that produces a first type of video signal based on a frame of color image-pixel-signals, a second video signal production system that produces a second type of video signal based on a frame of color image-pixel-signals processed by the color-balance alteration system, and a monitor system that is capable of selectively displaying a first image and a second image based on the first and second types of video signals, respectively.

Optionally, the electronic endoscope system may further comprise a display-mode selection system that selects either a first display mode or a second display mode, and a display control system that displays the first image on the monitor system based on the first type of video signal when the first display mode is selected by the display-mode selection system, and that displays the second image on the monitor system based on the second type of video signal when the second display mode is selected by the display-mode selection system.

Optionally, the electronic endoscope system may further comprise a disablement system that disables the color-balance alteration system when the first display mode is selected by the display-mode selection system, and an enablement system that enables the color-balance alteration system when the second display mode is selected by the display-mode selection system.

BRIEF DESCRIPTION OF THE DRAWINGS

The object and other objects of the present invention will be better understood from the following description, referring to the accompanying drawings, in which:

FIG. 4 is a conceptual view showing nine digital image-pixel-signals in a 3×3 matrix, produced in the color-balance alteration circuit;

DESCRIPTION OF THE PREFERRED EMBODIMENTS

Figure 1:
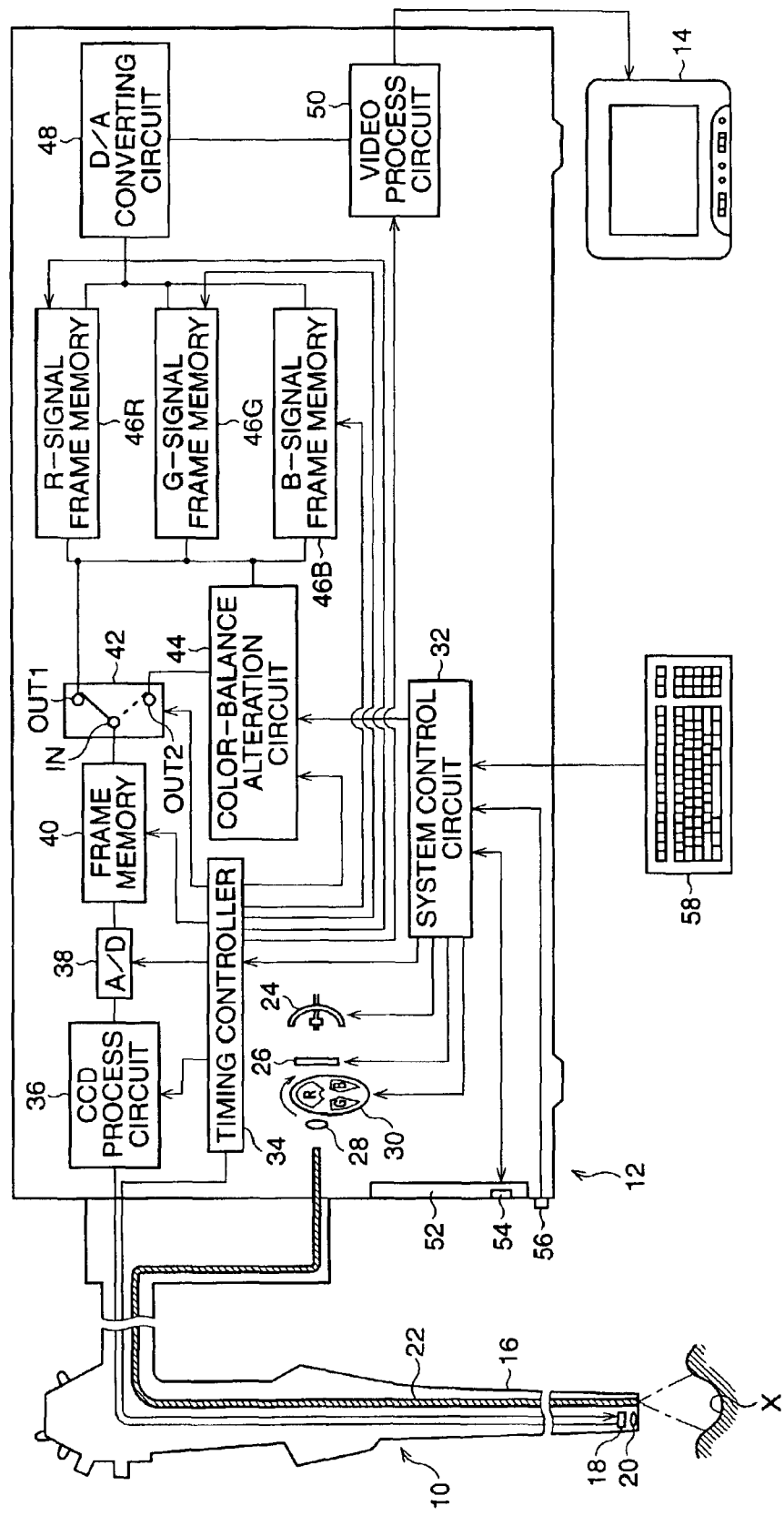
FIG. 1 is a schematic block diagram of a first embodiment of an electronic endoscope system according to the present invention.

Referring to FIG. 1, a first embodiment of an electronic endoscope system according to the present invention is shown as a block diagram. The electronic endoscope system comprises a video scope 10, an image-signal processing unit 12 to which the video scope 10 is detachably coupled, and a TV monitor 14 to which the image-signal processing unit 12 is connected. In this embodiment, at least two video scopes 10 use the image-signal processor 12 in common. This is because the scope 10 is detachably coupled to the image-signal processing unit 12.

The video scope 10 includes a flexible conduit 16 which is provided with a solid-state image sensor 18, such as a CCD (charge-coupled-device) image sensor, at the distal end thereof, and the CCD image sensor 18 is associated with an objective lens 20. When a connection is established between the video scope 10 and the image-signal processing unit 12, the CCD image sensor 18 is electrically connected to an image-signal processor provided in the image-signal processing unit 12.

Also, the video scope 10 includes a flexible optical light guide 22 which extends therethrough and which is formed as a bundle of optical fibers. The optical light guide 22 terminates with a light-radiating end face at the distal end of the flexible conduit 16, and is associated with a lighting lens system (not shown) provided thereat. When a connection is established between the video scope 10 and the image-signal processing unit 12, the proximal end of the optical light guide 22 is optically connected to a light source device provided in the image-signal processing unit 12, whereby the light, emitted from the light source device, radiates as an illuminating-light from the light-radiating end face of the optical light guide 22.

When the flexible conduit 16 of the video scope 10 is inserted in an organ of a patient, an illuminated object is focussed as an optical endoscope image on a light-receiving surface of the CCD image sensor 18, by the objective lens system 20 associated therewith. The focussed endoscope image is converted into a frame of analog image-pixel-signals by the CCD image sensor 18, and the frame of analog image-pixel-signals is sequentially read from the CCD image sensor 18. Then, the image-pixel-signals are fed to an image-signal processor provided in the image-signal processing unit 12, and a video signal is produced based on the image-pixel-signals, as discussed in detail hereinafter. Then, the video signal is fed from the image-signal processor to the TV monitor 14, and the endoscope image, sensed by the CCD image sensor 18, is reproduced as a motion picture on the TV monitor 14.

The light source device, provided in the image-signal processing unit 12, includes a white light lamp 24, such as a halogen lamp, a xenon lamp or the like, aligned with the proximal end of the light guide 22, a diaphragm 26 provided for adjusting an amount of light directed from the lamp 24 to the proximal end of the light guide 22, and a condenser lens 28 provided for focusing the light on the proximal end of the light guide 22.

In this embodiment, in order to reproduce an endoscope image as a full color motion picture on the TV monitor 14, an RGB field sequential-type color imaging method is used in the electronic endoscope system. To this end, the light source device further includes a rotary RGB color-filter 30 provided between the diaphragm 26 and the condenser lens 28, and the rotary RGB color-filter comprises a disk element having three sector-shaped color filters, i.e. red, green, and blue filters. These filters are circumferentially and uniformly arranged such that the three centers of the color filters are spaced at regular angular intervals of 120 degrees, and a sector area between the two adjacent color filters serves as a light-shielding area.

The rotary color-filter 30 is rotated at a given rotational frequency in accordance with a commonly used image-reproduction method, such as the NTSC method, the PAL method and so on. For example, in the NTSC method, the rotational frequency of the rotary color-filter 30 is 30 Hz, and, in the PAL method, the rotational frequency of the rotary color-filter 30 is 25 Hz.

Thus, during the rotation of the rotary color-filter 30, red, green, and blue lights are cyclically and sequentially made incident on the proximal end of the light guide 22, whereby the red, green, and blue lights are cyclically and sequentially emitted from the distal end face of the light guide 22. Namely, red, green, and blue endoscope images are sequentially and cyclically focused on the light-receiving surface of the CCD image sensor 18.

While the red, green, and blue endoscope images are cyclically focused on the light-receiving surface of the CCD image sensor 18 by the objective lens system 20, each of the red, green, and blue optical images is converted into a frame of monochromatic (red, green, blue) analog image-pixel-signals by the CCD image sensor 18. Each frame of monochromatic analog image-pixel-signals is read from the CCD image sensor 18 during the light-shielding time period which corresponds to the light-shielding area between two adjacent color filters of the rotary color-filter 30.

As shown in FIG. 1, the image-signal processing unit 12 is provided with a system control circuit 32 which controls the electronic endoscope system as a whole. The system control circuit 32 contains a microcomputer comprising a central processing unit (CPU), a read-only memory (ROM) for storing programs and constants, a random-access memory (RAM) for storing temporary data, and an input/output interface circuit (I/O). The image-signal processing unit 12 is further provided with a timing controller 34, which produces and outputs various series of clock pulses having given frequencies under the control of the system control circuit 32, thereby operating sequentially and systematically the aforesaid image-signal processor provided in the image-signal processing unit 12.

Note, as is apparent from FIG. 1, the turn-ON and turn-OFF of the lamp 24, the operation of the diaphragm 26, and the rotation of the rotary color-filter 30 are controlled by the system control circuit 32.

The image-signal processor, provided in the image-signal processing unit 12, includes a CCD process circuit 36. As shown in FIG. 1, when a connection is established between the video scope 10 and the image-signal processing unit 12, the CCD image sensor 18 is connected to the timing controller 34 and the CCD process circuit 36. The timing controller 34 produces and outputs a series of reading clock pulses to the CCD image sensor 18, whereby the three frames of monochromatic (red, green, and blue) analog image-pixel-signals are cyclically and sequentially read from the CCD image sensor 18. The read analog image-pixel-signals are fed to the CCD process circuit 36, in which the analog image-pixel-signals are subjected to various image-processings, such as gamma-correction, white-balance correction, profile-enhancing, noise-elimination, black-level-clamping and so on. For these various image-processings, the CCD process circuit 36 is operated in accordance with various series of clock pulses output from the timing controller 34.

The image-signal processor further includes an analog-to-digital (A/D) converter 38, a frame memory 40, a switching-circuit 42, a simulated dye-spraying process circuit or color-balance alteration circuit 44, an R-signal frame memory 46R, a G-signal frame memory 46G, a B-signal frame memory 46B, a digital-to-analog (D/A) converting circuit 48, and a video process circuit 50.

Each of the processed analog image-pixel-signals is output from the CCD process circuit 36 to the A/D converter 38, in which the analog image-pixel-signal concerned is converted into a digital image-pixel-signal. The conversion of the analog image-pixel-signal into the digital image-pixel-signal is performed in accordance with a series of sampling clock pulses output from the timing controller 34.

Then, the digital image-pixel-signal is temporarily stored in the frame memory 40. Namely, a frame of red digital image-pixel-signals, a frame of green digital image-pixel-signals, and a frame of blue digital image-pixel-signals are cyclically stored in the frame memory 40. While the digital image-pixel-signals are successively stored in the frame memory 40, the digital image-pixel-signals are read from the frame memory 40 in order.

Figure 2:
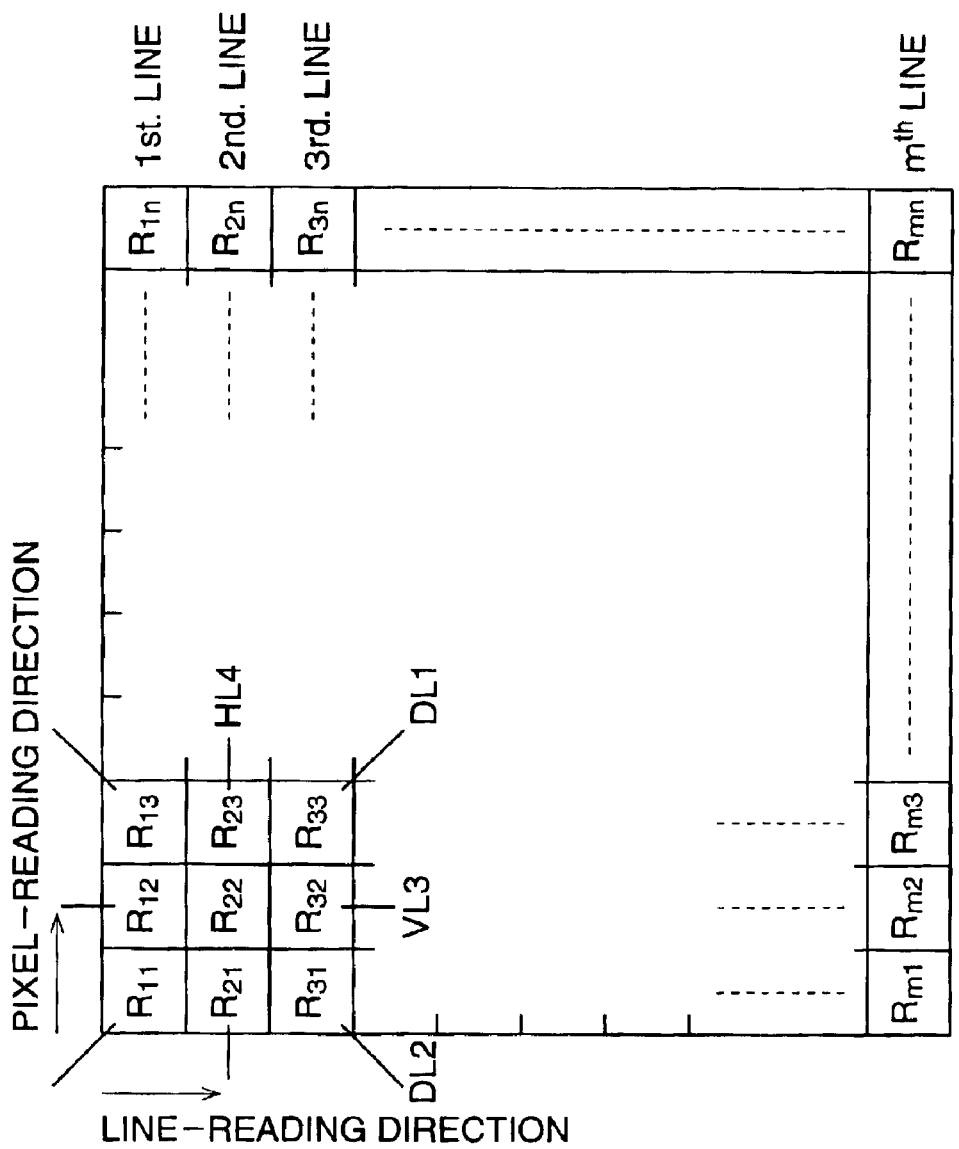
FIG. 2 is a conceptual view showing a frame of red digital image-pixel-signals stored in an m×n matrix manner in a frame memory used in the first embodiment of the electronic endoscope system.

FIG. 2 conceptually shows, by way of example, a frame of red digital image-pixel-signals $R_{11}$, $R_{12}$, ... $R_{m(n-1)}$, and $R_{mn}$, which are stored in a m×n matrix manner in the frame memory 40. Namely, a red image is formed by m lines, each of which includes n digital image-pixel-signals. The red digital image-pixel-signals $R_{11}$, $R_{12}$, ... $R_{m(n-1)}$, and $R_{mn}$ are read from the frame memory 40 in a line-reading direction and in a pixel-reading direction indicated by the arrows in FIG. 2, and are then fed to the switching-circuit 42. In this embodiment, each of the digital image-pixel-signals $R_{11}$, $R_{12}$, ... $R_{m(n-1)}$, and $R_{mn}$ is composed of eight bits, and represents any one of 256 values. The same is true for the green digital image-pixel-signals $G_{11}$, $G_{12}$, ... $G_{m(n-1)}$, and $G_{mn}$, and the blue digital image-pixel-signals $B_{11}$, $B_{12}$, ... $B_{m(n-1)}$ and $B_{mn}$.

Note, the storage of the digital image-pixel-signals in the frame memory 40 is performed in accordance with a series of writing-clock pulses output from the timing controller 34, and the reading of the digital image-pixel-signals from the frame memory 40 is performed in accordance with a series of reading-clock pulses.

The switching-circuit 42 has an input terminal "IN", a first output terminal "OUT1", and a second output terminal "OUT2". The switching of the connection of the input terminal "IN" from the first output terminal "OUT1" to the second output terminal "OUT2" and vice versa is performed by a switching pulse output from the timing controller 34. Namely, usually, the pulse output from the timing controller 34 to the switching-circuit 42 is maintained at a low level to thereby establish the connection between the input terminal "IN" and the first output terminal "OUT1". When a high-level switching pulse is output from the timing controller 34 to the switching-circuit 42, the connection of the input terminal "IN" is switched from the first output terminal "OUT1" to the second output terminal "OUT2", and the connection between the input terminal "IN" and the second output terminal "OUT2" is maintained over a duration corresponding to the output of the high-level switching pulse.

In this embodiment, either a usual display mode or a simulated dye-spraying display mode is selected. When the usual display mode is selected, the input terminal "IN" is connected to the first output terminal "OUT1", such that the digital image pixel-signal, read from the frame memory 40, is directly output from the first output terminal "OUT1" to any one of the R-signal, G-signal, and B-signal frame memories 46R, 46G, and 46B. Namely, when the digital image pixel-signal is red, it is stored in the R-signal frame memory 46R; when the digital image pixel-signal is green, it is stored in the G-signal frame memory 46G; and when the digital image pixel-signal is blue, it is stored in the B-signal frame memory 46B.

When the simulated dye-spraying display mode is selected, the connection of the input terminal "IN" is switched from the first output terminal "OUT1" to the second output terminal "OUT2", such that the respective frames of red and green image-pixel-signals are fed from the frame memory 40 to the red-signal and green-signal frame memories 46R and 46G through the color-balance alteration circuit 44, and such that the frame of blue image-pixel-signals is directly fed to and stored in the blue-signal frame memory 46B. Namely, in the simulated-dye-spraying display mode, the frames of red and green image-pixel-signals are read from the frame memory 40, only when the input terminal "IN" is connected to the output terminal "OUT2". More precisely, when the simulated dye-spraying display mode is selected, only the frames of red and green image-pixel-signals are subjected to a color-balance alteration process in the color-balance alteration circuit 44, as explained in detail hereinafter. The processed red and green image-pixel-signals are respectively fed to and stored in the red-signal and green-signal frame memories 46R and 46G.

Note, the storage of the digital image-pixel-signals in each frame memory (46R, 46G, 46) is performed in accordance with a series writing clock pulses output from the timing controller 34.

The red, green, and blue digital image-pixel-signals are simultaneously read from the R-signal, G-signal, and B-signal frame memories 46R, 46G, and 46B, and are output to the D/A converting circuit 48. The D/A converting circuit 48 includes three digital-to-analog (D/A) converters, and the respective red, green, and blue digital image-pixel-signals are simultaneously converted into red, green, and blue analog image signals by the three D/A converters.

Then, the red, green, and blue analog image signals are output from the D/A converting circuit 48 to the video process circuit 50. On the other hand, the timing controller 34 produces a composite synchronizing signal, and the composite synchronizing signal is output from the timing controller 34 to the video process circuit 50. Thus, the video process circuit 50 produces a component type video signal based on the red, green, and blue image signals output from the D/A converting circuit 48, and the synchronizing signal output from the timing controller 34.

In the video process circuit 50, the component type video signal is subjected to various image-processings, such as high frequency noise-elimination, profile-enhancing, and so on. Then, the processed component type video signal is fed from the video process circuit 50 to the TV video monitor 14. Thus, an optical endoscope image, successively captured by the CCD image sensor 18, is reproduced as a full color motion picture on the TV monitor 14.

While the usual display mode is selected, the endoscope image is reproduced on the TV monitor 14 with a given proper color balance. However, while the simulated dye-spraying display mode is selected, the endoscope image is observed on the TV monitor 14 as if it were sprayed with a blue-solution, due to the color-balance alteration process of the red and green digital image-pixel-signals in the color-balance alteration circuit 44, as stated hereinafter.

Note, the video process circuit 50 may include a color encoder for producing various video signals, such as, a S-video signal, a composite type video signal and so on, based on the component type video signal.

In FIG. 1, reference 52 indicates a front panel attached to a front wall of a housing of the image-signal processing unit 12, and the front panel 52 includes various switches. A switch, which especially relates to the present invention, is a display-mode selection switch 54. Also, reference 56 indicates a power ON/OFF switch provided on the front wall of the housing of the image-signal processing unit 12.

The display-mode selection switch 54 is provided for selecting either the usual display mode or the simulated dye-spraying display mode. The display-mode selection switch 54 is constituted to alternately output a high-level signal or a low-level signal to the system control circuit 32 whenever it is operated. When the high-level signal is output from the display-mode selection switch 54, the system control circuit 32 recognizes that the simulated dye-spraying display mode has been selected. When the low-level signal is output from the display-mode selection switch 54, the system control circuit 32 recognizes that the usual display mode has been selected. In short, whenever the display-mode selection switch 54 is operated, the usual display mode or the simulated-dye-spraying display mode is changed from one to the other.

When the power ON/OFF switch 56 is turned ON, the image-signal processing unit 12 is supplied with electric power from a commercial power source. Note, when the power ON/OFF switch 56 is turned ON, the low-level signal is output from the display-mode selection switch 54, and the usual display mode is forcibly selected.

As shown in FIG. 1, a keyboard 58 is connected to the system control circuit 32 of the image-signal processing unit 12 to input various commands and various data to the system control circuit 32. A function, pertaining to the display-mode selection switch 54, may be allocated to a function key on the keyboard 58. When the display-mode selection is performed by the function key on the keyboard 58, the display-mode selection switch 54 may be eliminated from the front panel 52.

Figure 3:
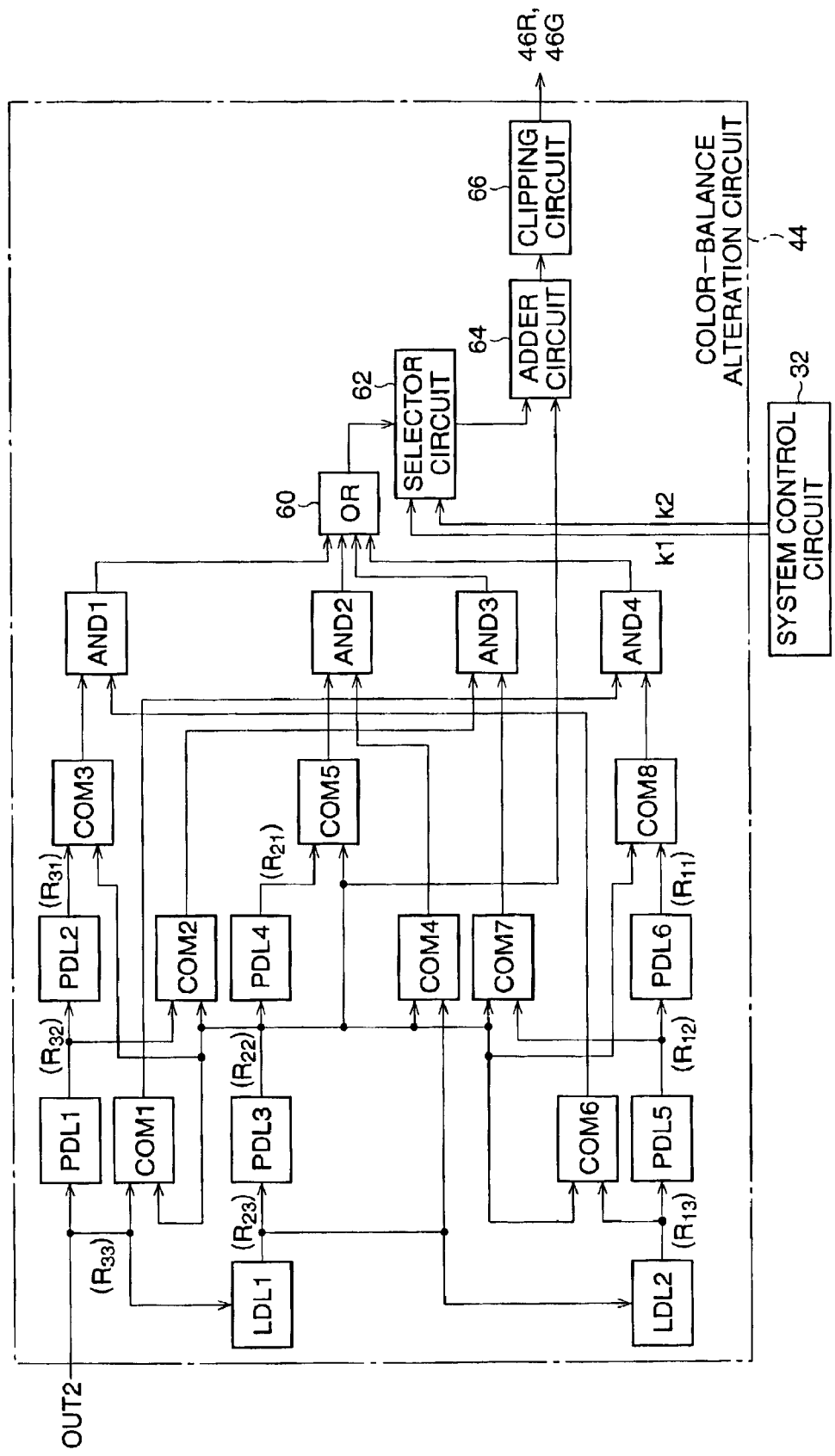
FIG. 3 is a schematic block diagram of a color-balance alteration circuit used as a simulated dye-spraying process circuit in the first embodiment of the electronic endoscope system.

Referring to FIG. 3, the color-balance alteration circuit 44 is shown as a block diagram. The color-balance alteration circuit 44 comprises a delay-circuit arrangement, a comparator arrangement, and an AND-gate arrangement. In particular, the delay circuit arrangement includes first and second one-line delay circuits "LDL1" and "LDL2", and first, second, third, fourth, fifth, and sixth one-pixel delay circuits "PDL1", "PDL2", "PDL3", "PDL4", "PDL5" and "PDL6"; the comparator arrangement includes first, second, third, fourth, fifth, sixth, seventh, and eighth comparators "COM1", "COM2", "COM3", "COM4", "COM5", "COM6", "COM7", and "COM8"; and the AND-gate arrangement includes first, second, third, and fourth AND-gates "AND1", "AND2", "AND3", and "AND4", with these elements being wired and arranged as shown in FIG. 3.

As already stated, in the simulated-dye-spraying display mode, the frames of red and green image-pixel-signals are read from the frame memory 40, only when the input terminal "IN" of the switching-circuit 42 is connected to the second output terminal "OUT2", such that only the frames of red and green image-pixel-signals are fed from the frame memory 40 to the color-balance alteration circuit 44. Thus, as is apparent from FIG. 3, a red or green digital image-pixel-signal, read from the frame memory 40, is input to the first one-line delay circuit "LDL1", the first one-pixel delay circuit "PDL1", and the first comparator "COM1".

The first one-line delay circuit "LDL1" outputs the input digital image-pixel-signal after a time necessary for reading one line of digital image-pixel-signals from the frame memory 40 has elapsed. Namely, the outputting of the digital image-pixel-signal from the first one-line delay circuit "LDL1" is delayed for the reading time of the one line of digital image-pixel-signals. The same is true for the second one-line delay circuit "LDL2".

On the other hand, the first one-pixel delay circuit "PDL1" outputs the input digital image-pixel-signal after a time necessary for reading one digital image-pixel-signal from the frame memory 40 has elapsed. Namely, the outputting of the digital image-pixel-signal from the first one-pixel delay circuit "PDL1" is delayed for the reading time of the one digital image-pixel-signal. The same is true for each of the remaining one-pixel delay circuits "PDL2", "PDL3", "PDL4", "PDL5", and "PDL6".

Thus, for example, while the red digital image-pixel-signals $R_{11}$, $R_{12}$, ... $R_{m(n-1)}$, and $R_{mn}$ are successively fed one by one from the frame memory 40 to the color-balance alteration circuit 44, a set of nine red digital image-pixel-signals $R_{(i-1)(j-1)}$, $R_{(i-1)j}$, $R_{(i-1)(j+1)}$, $R_{i(j-1)}$, $R_{ij}$, $R_{i(j+1)}$, $R_{(i+1)(j-1)}$, $R_{(i+1)j}$, and $R_{(i+1)(j+1)}$ is produced in the delay-circuit arrangement ($2 \leq i \leq (m-1)$, $2 \leq j \leq (n-1)$). Namely, these nine red digital image-pixel-signals form a 3×3 matrix in the delay circuit arrangement, as shown in FIG. 4.

In particular, when the pixel-signal $R_{(i+1)(j+1)}$ is fed from the frame memory 40 to the color-balance alteration circuit 44, the pixel-signal $R_{(i-1)(j-1)}$ is output from the sixth one-pixel delay circuit "PDL6"; the pixel-signal $R_{(i-1)j}$ is output from the fifth one-pixel delay circuit "PDL5"; the pixel-signal $R_{(i-1)(j+1)}$ is output from the second one-line delay circuit "LDL2"; the pixel-signal $R_{i(j-1)}$ is output from the fourth one-pixel delay circuit "PDL4"; the pixel-signal $R_{ij}$ is output from the third one-pixel delay circuit "PDL3"; the pixel-signal $R_{i(j+1)}$ is output from the second one-line delay circuit "LDL1"; the pixel-signal $R_{(i+1)(j-1)}$ is output from the second one-pixel delay circuit "PDL2"; and the pixel-signal $R_{(i+1)j}$ is output from the first one-pixel delay circuit "PDL1". As shown in FIG. 4, the pixel-signal $R_{ij}$, output from the third one-pixel delay circuit "PDL3", forms a central pixel-signal surrounded by the remaining eight circumferential pixel-signals $R_{(i-1)(j-1)}$, $R_{(i-1)j}$, $R_{(i-1)(j+1)}$, $R_{i(j-1)}$, $R_{i(j+1)}$, $R_{(i+1)(j-1)}$, $R_{(i+1)j}$, and $R_{(i+1)(j+1)}$.

For example, when the red digital image-pixel-signal $R_{33}$ is fed from the frame memory 40 to the color-balance alteration circuit 44, the red digital image-pixel-signals $R_{32}$ and $R_{31}$ are respectively output from the first and second one-pixel delay circuits "PDL1" and "PDL2"; the red digital image-pixel-signals $R_{23}$, $R_{22}$, and $R_{21}$ are respectively output from the first one-line delay circuit "LDL1" and the third and fourth one-pixel delay circuits "PDL3" and "PDL4"; and the red digital image-pixel-signals $R_{13}$, $R_{12}$, and $R_{11}$ are respectively output from the second one-line delay circuit "LDL2" and the fifth and sixth one-pixel delay circuits "PDL5" and "PDL6". In this case, as shown in FIG. 2, the pixel-signal $R_{22}$ ($R_{ij}$) or central pixel-signal is surrounded by the other eight circumferential pixel-signals $R_{11}$, $R_{12}$, $R_{13}$, $R_{21}$, $R_{23}$, $R_{31}$, $R_{32}$, and $R_{33}$.

As shown in FIG. 3, each of the comparators "COM1" to "COM8" has two input terminals and an output terminal. The central pixel-signal $R_{mn}$ ($R_{22}$) is input to one of the two input terminals of each comparator "COM1" to "COM8" when the pixel-signal $R_{(m+1)(n+1)}$ ($R_{33}$) is fed from the frame memory 40 to the color-balance alteration circuit 44.

Also, each of the AND-gates "AND1" to "AND4" has two input terminals which are connected to output terminals of two comparators selected from among the comparators "COM1" to "COM8". In particular, the input terminals of the first AND-gate "AND1" are connected to the output terminals of the third and sixth comparators "COM3" and "COM6"; the input terminals of the second AND-gate "AND2" are connected to the output terminals of the fourth and fifth comparators "COM4" and "COM5"; the input terminals of the third AND-gate "AND3" are connected to the output terminals of the second and seventh comparators "COM2" and "COM7"; and the input terminals of the fourth AND-gate "AND4" are connected to the output terminals of the first and eighth comparators "COM1" and "COM8".

As is apparent from the arrangement of FIG. 3, for example, when the pixel-signal $R_{33}$ is fed from the frame memory 40 to the color-balance alteration circuit 44, it is input to the other output terminal of the first comparator "COM1", in which the signal-level of the pixel-signal $R_{33}$ is compared with that of the central pixel-signal $R_{22}$. When the signal-level of the pixel-signal $R_{33}$ is higher than that of the central pixel-signal $R_{22}$, the first comparator "COM1" outputs a high-level signal "1" from its output terminal to the fourth AND-gate "AND4". When the signal-level of the pixel-signal $R_{33}$ is equal to or lower than that of the central pixel-signal $R_{22}$, the first comparator "COM1" outputs a low-level signal "0" from its output terminal to the fourth AND-gate "AND4".

On the other hand, the pixel-signal $R_{11}$, output from the sixth one-pixel delay circuit "PDL6", is input to the other output terminal of the eighth comparator "COM8", in which the signal-level of the pixel-signal $R_{11}$ is compared with that of the central pixel-signal $R_{22}$. When the signal-level of the pixel-signal $R_{11}$ is higher than that of the central pixel-signal $R_{22}$, the eighth comparator "COM8" outputs a high-level signal "1" from its output terminal to the fourth AND-gate "AND4". When the signal-level of the pixel-signal $R_{11}$ is equal to or lower than that of the central pixel-signal $R_{22}$, the eighth comparator "COM8" outputs a low-level signal "0" from its output terminal to the fourth AND-gate "AND4".

Thus, only when both the signal-levels of the pixel-signals $R_{11}$ and $R_{33}$ are higher than that of the central pixel-signal $R_{22}$, does the fourth AND-gate "AND4" output a high-level signal "1" from its output terminal. When a signal-level of either of the pixel-signals $R_{11}$ and $R_{33}$ is lower than that of the central pixel-signal $R_{22}$, the fourth AND-gate "AND4" outputs a low-level signal "0" from its output terminal.

As is apparent from FIG. 2, the pixel-signals $R_{11}$, $R_{22}$, and $R_{33}$ are aligned with each other along a diagonal line "DL1" on the 3×3 matrix. For example, supposing that a mucous membrane of a stomach is observed by the electronic endoscope system, and that the stomach is cut along a line corresponding to the diagonal line "DL1", the output of the high-level signal "1" from the fourth AND-gate "AND4" means that an area, from which the central pixel-signal $R_{22}$ is derived, is regarded as a fine recess area X on the stomach mucous membrane surface, as shown conceptually and symbolically in FIG. 1, because both the signal-levels of the pixel-signals $R_{11}$ and $R_{33}$ are higher than that of the central pixel-signal $R_{22}$. On the other hand, the output of the low-level signal "0" from the fourth AND-gate "AND4" means that an area, from which the central pixel-signal $R_{22}$ is derived, cannot be regarded as the fine recess area on the stomach mucous membrane surface, because at least one of the signal-levels of the pixel-signals $R_{11}$ and $R_{33}$ is equal to or lower than that of the central pixel-signal $R_{22}$.

The pixel-signal $R_{31}$, output from the second one-pixel delay circuit "PDL2", is input to the other output terminal of the third comparator "COM3", in which a signal-level of the pixel-signal $R_{31}$ is compared with that of the central pixel-signal $R_{22}$. When the signal-level of the pixel-signal $R_{31}$ is higher than that of the central pixel-signal $R_{22}$, the third comparator "COM3" outputs a high-level signal "1" from its output terminal to the first AND-gate "AND1". When the signal-level of the pixel-signal $R_{31}$ is equal to or lower than that of the central pixel-signal $R_{22}$, the third comparator "COM3" outputs a low-level signal "0" from its output terminal to the first AND-gate "AND1".

On the other hand, the pixel-signal $R_{13}$, output from the second one-line delay circuit "LDL2", is input to the other output terminal of the sixth comparator "COM6", in which a signal-level of the pixel-signal $R_{13}$ is compared with that of the central pixel-signal $R_{22}$. When the signal-level of the pixel-signal $R_{13}$ is higher than that of the central pixel-signal $R_{22}$, the sixth comparator "COM6" outputs a high-level signal "1" from its output terminal to the first AND-gate "AND1". When the signal-level of the pixel-signal $R_{13}$ is equal to or lower than that of the central pixel-signal $R_{22}$, the sixth comparator "COM6" outputs a low-level signal "0" from its output terminal to the first AND-gate "AND1".

Thus, only when both the signal-levels of the pixel-signals $R_{13}$ and $R_{31}$ are higher than that of the central pixel-signal $R_{22}$, does the first AND-gate "AND1" output a high-level signal "1" from its output terminal. When at least one of the signal-levels of the pixel-signals $R_{13}$ and $R_{31}$ is lower than that of the central pixel-signal $R_{22}$, the first AND-gate "AND1" outputs a low-level signal "0" from its output terminal.

As is apparent from FIG. 2, the pixel-signals $R_{13}$, $R_{22}$, and $R_{31}$ are aligned with each other along another diagonal line "DL2" on the 3×3 matrix. Similar to the aforesaid case, the output of the high-level signal "1" from the first AND-gate "AND1" means that the area, from which the central pixel-signal $R_{22}$ is derived, is regarded as a fine recess area on the stomach mucous membrane surface, because both the signal-levels of the pixel-signals $R_{13}$ and $R_{31}$ are higher than that of the central pixel-signal $R_{22}$. On the other hand, the output of the low-level signal "0" from the first AND-gate "AND1" means that the area, from which the central pixel-signal $R_{22}$ is derived, cannot be regarded as the fine recess area, because at least one of the signal-levels of the pixel-signals $R_{13}$ and $R_{31}$ is equal to or lower than that of the central pixel-signal $R_{22}$.

The pixel-signal $R_{32}$, output from the first one-pixel delay circuit "PDL1", is input to the other output terminal of the second comparator "COM2", in which the signal-level of the pixel-signal $R_{32}$ is compared with that of the central pixel-signal $R_{22}$. When the signal-level of the pixel-signal $R_{32}$ is higher than that of the central pixel-signal $R_{22}$, the second comparator "COM2" outputs a high-level signal "1" from its output terminal to the third AND-gate "AND3". When the signal-level of the pixel-signal $R_{32}$ is equal to or lower than that of the central pixel-signal $R_{22}$, the second comparator "COM2" outputs a low-level signal "0" from its output terminal to the third AND-gate "AND3".

On the other hand, the pixel-signal $R_{12}$, output from the fifth one-pixel delay circuit "PDL5", is input to the other output terminal of the seventh comparator "COM7", in which the signal-level of the pixel-signal $R_{12}$ is compared with that of the central pixel-signal $R_{22}$. When the signal-level of the pixel-signal $R_{12}$ is higher than that of the central pixel-signal $R_{22}$, the seventh comparator "COM7" outputs a high-level signal "1" from its output terminal to the third AND-gate "AND3". When the signal-level of the pixel-signal $R_{12}$ is equal to or lower than that of the central pixel-signal $R_{22}$, the seventh comparator "COM7" outputs a low-level signal "0" from its output terminal to the third AND-gate "AND3".

Thus, only when both the signal-levels of the pixel-signals $R_{12}$ and $R_{32}$ are higher than that of the central pixel-signal $R_{22}$, does the third AND-gate "AND3" output a high-level signal "1" from its output terminal. When at least one of the signal-levels of the pixel-signals $R_{12}$ and $R_{32}$ is lower than that of the central pixel-signal $R_{22}$, the third AND-gate "AND3" outputs a low-level signal "0" from its output terminal.

As is apparent from FIG. 2, the pixel-signals $R_{12}$, $R_{22}$, and $R_{32}$ are aligned with each other along a vertical line "VL3" on the 3×3 matrix. Similar to the aforesaid cases, the output of the high-level signal "1" from the third AND-gate "AND3" means that the area, from which the central pixel-signal $R_{22}$ is derived, is regarded as the fine recess area on the stomach mucous membrane surface, because both the signal-levels of the pixel-signals $R_{12}$ and $R_{32}$ are higher than that of the central pixel-signal $R_{22}$. On the other hand, the output of the low-level signal "0" from the first AND-gate "AND1" means that the area, from which the central pixel-signal $R_{22}$ is derived, cannot be regarded as the fine recess area, because at least one of the signal-levels of the pixel-signals $R_{12}$ and $R_{32}$ is equal to or lower than that of the central pixel-signal $R_{22}$.

The pixel-signal $R_{23}$, output from the first one-line delay circuit "LDL1", is input to the other output terminal of the fourth comparator "COM4", in which the signal-level of the pixel-signal $R_{23}$ is compared with that of the central pixel-signal $R_{22}$. When the signal-level of the pixel-signal $R_{23}$ is higher than that of the central pixel-signal $R_{22}$, the fourth comparator "COM4" outputs a high-level signal "1" from its output terminal to the second AND-gate "AND2". When the signal-level of the pixel-signal $R_{23}$ is equal to or lower than that of the central pixel-signal $R_{22}$, the fourth comparator "COM4" outputs a low-level signal "0" from its output terminal to the second AND-gate "AND2".

On the other hand, the pixel-signal $R_{21}$, output from the fourth one-pixel delay circuit "PDL4", is input to the other output terminal of the fifth comparator "COM5", in which the signal-level of the pixel-signal $R_{21}$ is compared with that of the central pixel-signal $R_{22}$. When the signal-level of the pixel-signal $R_{21}$ is higher than that of the central pixel-signal $R_{22}$, the fifth comparator "COM5" outputs a high-level signal "1" from its output terminal to the second AND-gate "AND2". When the signal-level of the pixel-signal $R_{21}$ is equal to or lower than that of the central pixel-signal $R_{22}$, the fifth comparator "COM5" outputs a low-level signal "0" from its output terminal to the second AND-gate "AND2".

Thus, only when both the signal-levels of the pixel-signals $R_{21}$ and $R_{23}$ are higher than that of the central pixel-signal $R_{22}$, does the second AND-gate "AND2" output a high-level signal "1" from its output terminal. When at least one of the signal-levels of the pixel-signals $R_{21}$ and $R_{23}$ is lower than that of the central pixel-signal $R_{22}$, the second AND-gate "AND2" outputs a low-level signal "0" from its output terminal.

As is apparent from FIG. 2, the pixel-signals $R_{21}$, $R_{22}$, and $R_{23}$ are aligned with each other along a horizontal line "HL4" on the 3×3 matrix. Similar to the aforesaid cases, the output of the high-level signal "1" from the second AND-gate "AND2" means that the area, from which the central pixel-signal $R_{22}$ is derived, is regarded as the fine recess area on the stomach mucous membrane surface, because both the signal-levels of the pixel-signals $R_{21}$ and $R_{23}$ are higher than that of the central pixel-signal $R_{22}$. On the other hand, the output of the low-level signal "0" from the second AND-gate "AND2" means that the area, from which the central pixel-signal $R_{22}$ is derived, cannot be regarded as the fine recess area, because at least one of the signal-levels of the pixel-signals $R_{21}$ and $R_{23}$ is equal to or lower than that of the central pixel-signal $R_{22}$.

As shown in FIG. 3, the color-balance alteration circuit 44 also comprises an OR-gate circuit 60, and a selector circuit 62. The OR-gate circuit 60 has four input terminals connected to the four output terminals of the AND-gates "AND1" to "AND4", and the output terminal of the OR-gate circuit 60 is connected to the selector circuit 62.

When any one of the AND-gates "AND1" to "AND4" outputs the high-level signal "1", i.e. when the area, from which the central pixel-signal $R_{22}$ is derived, is regarded as the fine recess area along any one of the lines DL1, DL2, VL3, and HL4, the OR-gate circuit 60 outputs a high-level signal "1" to the selector circuit 62. When all the AND-gates "AND1" to "AND4" output the low-level signal "0", i.e. when the area, from which the central pixel-signal $R_{22}$ is derived, cannot be regarded as the fine recess area, the OR-gate circuit 60 outputs a low-level signal "0" to the selector circuit 62.

As is apparent from in FIG. 3, a first constant "k1" and a second constant "k2" are output from the system control circuit 32 to the selector circuit 62, and either the first constant "k1" or the second constant "k2" is selectively output from the selector circuit 62 in accordance with an output signal-level of the OR-gate circuit 60. Namely, when the low-level signal "0" is input from the OR-gate circuit 60 to the selector circuit 62, the first constant "k1" is output from the selector circuit 62. When the high-level signal "1" is input from the OR-gate circuit 60 to the selector circuit 62, the second constant "k2" is output from the selector circuit 62. A setting of "0" is always given to the first constant "k1", and a setting of a minus value, for example, "−50" is given to the second constant "k2".

Note, although the values of the first and second constants "k1" and "k2" are conveniently represented by the decimal numbers, in reality, each absolute value of the first constants "k1" and "k2" should be represented by an eight-bit binary number because each of the digital image-pixel-signals is composed of eight bits. Namely, the first constant "k1" is [00000000], and the absolute value of the second constant "k2" is [00110010] corresponding to the decimal number of "50".

As shown in FIG. 3, the color-balance alteration circuit 44 further comprises an adder circuit 64, and a clipping circuit 66. While either the first constant "k1" or the second constant "k2" is output from the selector circuit 62 and input to the adder circuit 64, the central pixel-signal $R_{22}$ is output from the third one-pixel delay circuit "PDL3" and input to the adder circuit 64. Thus, in the adder circuit 64, either the first constant "k1" or the second constant "k2" is added to the level value of the central pixel-signal $R_{22}$.

In particular, when the area, from which the central pixel-signal $R_{22}$ is derived, is regarded as the fine recess area, the absolute value of the second constant "k2 (−50)" is subtracted from the level value of the central pixel-signal $R_{22}$, and the central pixel-signal $R_{22}$, having the reduced signal level, is output from the adder circuit 64 to the clipping circuit 66. On the other hand, when the area, from which the central pixel-signal $R_{22}$ is derived, cannot be regarded as the fine recess area, the central pixel-signal $R_{22}$ is output from the adder circuit 64 to the clipping circuit 66 as it presently stands, because the first constant "k1" is zero.

In the clipping circuit 66, a zero is set as a clipping level such that only the pixel-signal ($R_{22}$), having a plus signal level, passes through the clipping circuit 66 as it stands. Namely, when the pixel-signal ($R_{22}$), output from the adder circuit 64, is either zero or minus, it is output as a zero level signal from the clipping circuit 66. The central pixel-signal ($R_{22}$), output from the clipping circuit 66, is fed to the R-signal frame memory 46R.

In short, when the area, from which a central red image-pixel-signal $R_{ij}$ is derived, is regarded as a fine recess area, the signal level of the central red image-pixel-signal $R_{ij}$ is reduced by the absolute value of the second constant "k2". The same is true for the green digital image-pixel-signals $G_{11}, G_{12}, \ldots G_{m(n-1)}$, and $G_{mn}$. Namely, when the area, from which a central green image-pixel-signal $G_{ij}$ is derived, is regarded as a fine recess area, the signal level of the central green image-pixel-signal $G_{ij}$ is reduced by the absolute value of the second constant "k2".

Accordingly, in the simulated dye-spraying display mode, when the color image-pixel-signals $R_{ij}$, $G_{ij}$, and $B_{ij}$ are derived from the fine recess area, the respective signal-level values of the red and green image-pixel-signals $R_{ij}$ and $G_{ij}$ are decreased by the absolute value of the second constant "k2", but the signal-level value of the blue image-pixel-signal $B_{ij}$ cannot be deceased because the blue image-pixel-signal $B_{ij}$ is directly written and stored in the B-signal frame memory 46B without being fed to the color-balance alteration circuit 44, as stated before. Thus, while the simulated dye-spraying display mode is selected, a color image-pixel on the TV monitor 14, represented by the color image-pixel-signals $R_{ij}$, $G_{ij}$, and $B_{ij}$, becomes bluish. Namely, a bluish endoscope image is observed on the TV monitor 14 as if an endoscope image, sensed by the CCD image sensor 18, were sprayed with a blue-solution.

As is apparent from the foregoing, according to the present invention, since the fine recess area is detected by comparing the central image-pixel-signal ($R_{ij}$, $G_{ij}$) with the two image-signal pixels aligned with the central image-pixel-signal ($R_{ij}$, $G_{ij}$) along each line (DL1, DL2, VH3, HL4) on the 3×3 matrix (FIG. 2), it is possible to properly perform the detection of the fine recess area, even though three aligned image-pixel-signals on the 3×3 matrix are lie on a fine groove, or even though the fine recess area to be detected is adjacent to one or more fine deep recess areas.

Figure 5:
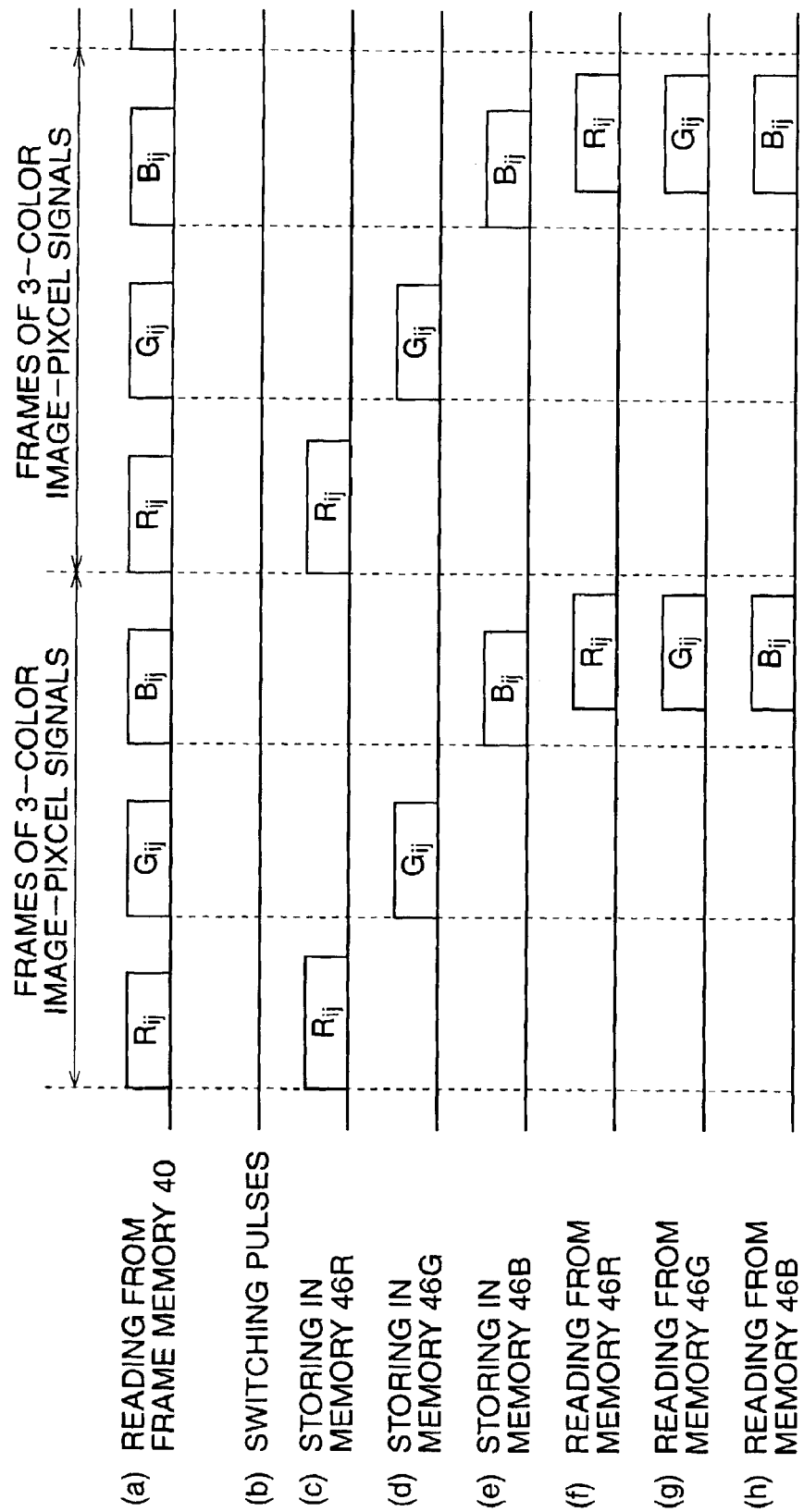
FIG. 5 is an operational timing chart for explaining an operation of the first embodiment of the electronic endoscope system in a usual display mode.

FIG. 5 shows an operational timing chart of the electronic endoscope during the selection of the usual display mode.

Three frames of color (red, green, and blue) digital image-pixel-signals ($R_{ij}$, $G_{ij}$ and $B_{ij}$) are cyclically and sequentially read from the frame memory 40, as indicated by item (a) in the timing chart of FIG. 5. In the usual display mode, since the output from the timing controller 34 to the switching-circuit 42 is maintained at the low level, as indicated by item (b) in the timing chart of FIG. 5, the connection is established between the input terminal "IN" and the first output terminal "OUT1" in the switching-circuit 42. Thus, the frames of red, green, and blue digital image-pixel-signals ($R_{ij}$, $G_{ij}$, and $B_{ij}$) are cyclically and sequentially stored in the R-signal, G-signal, and B-signal frame memories 40R, 40G, and 40B, as indicated by items (c), (d), and (e) in the timing chart of FIG. 5. Then, the frames of red, green, and blue digital image-pixel-signals ($R_{ij}$, $G_{ij}$, and $B_{ij}$) are simultaneously read from the frame memories 46R, 46G, and 46B, as indicated by items (f), (g), and (h) in the timing chart of FIG. 5, to reproduce the endoscope image on the TV monitor 14 in the usual display mode.

Figure 6:
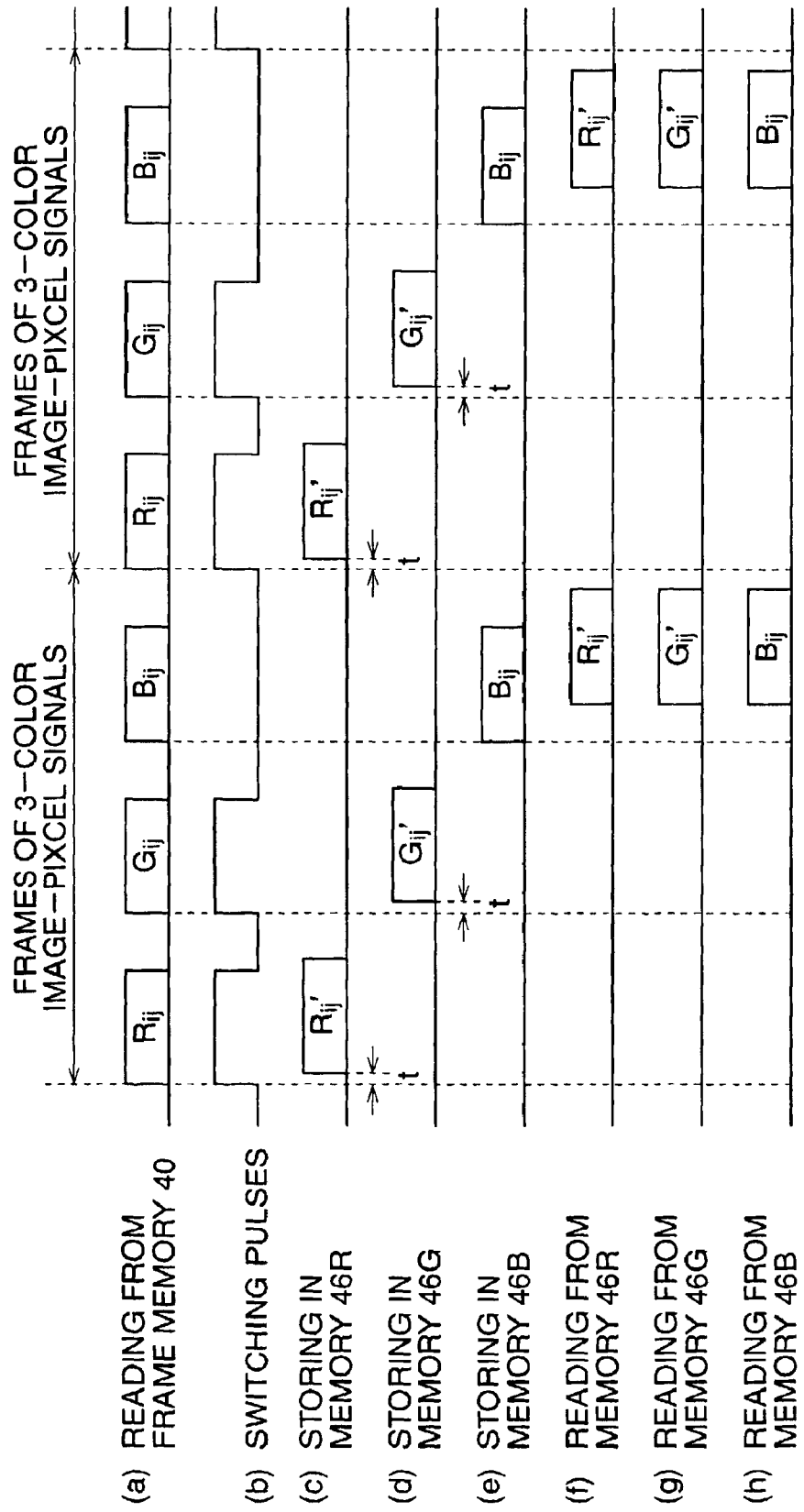
FIG. 6 is an operational timing chart for explaining an operation of the first embodiment of the electronic endoscope system in a simulated-dye-spraying display mode.

FIG. 6 shows another operational timing chart of the electronic endoscope during the selection of the simulated-dye-spraying display mode.

Similarly, three frames of color (red, green, and blue) digital image-pixel-signals ($R_{ij}$, $G_{ij}$, and $B_{ij}$) are cyclically and sequentially read from the frame memory 40, as indicated by item (a) in the timing chart of FIG. 6. In the simulated-dye-spraying display mode, the switching pulses are output from the timing controller 34 to the switching-circuit 42, as indicated by item (b) in the timing chart of FIG. 6. Namely, the outputting of the switching pulses is synchronized with the reading of the frames of red and green digital image-pixel-signals ($R_{ij}$ and $G_{ij}$) from the frame memory 40. As stated above, the connection of the input terminal "IN" is switched from the first output terminal "OUT1" to the second output terminal "OUT2" every time the high-level switching pulse is output, and the connection between the input terminal "IN" and the second output terminal "OUT2" is maintained over a duration corresponding to the output of the high-level switching pulse.

Thus, only the frames of red and green digital image-pixel-signals ($R_{ij}$ and $G_{ij}$), read from the frame memory 40, are fed to the color-balance alteration circuit 44, and are subjected to the color-balance alteration process, as already explained. Then, the processed red and green digital image-pixel-signals ($R_{ij}'$ and $G_{ij}'$) are stored in the R-signal and G-signal frame memories 40R and 40G, as indicated by items (c) and (d) in the timing chart of FIG. 6. On the other hand, the frame of blue digital image-pixel-signals ($B_{ij}$) is directly stored in the B-signal frame memory 46B, as indicated by item (e) in the timing chart of FIG. 6, because the output from the timing controller 34 to the switching-circuit 42 is maintained at the low level during the reading of the frame of blue digital image-pixel-signal from the frame memory 40, as indicated by item (b) in the timing chart of FIG. 6. Subsequently, the frames of red, green, and blue digital image-pixel-signals ($R_{ij}'$, $G_{ij}'$, and $B_{ij}$) are simultaneously read from the frame memories 46R, 46G, and 46B, as indicated by items (f), (g), and (h) in the timing chart of FIG. 6, to reproduce the endoscope image on the TV monitor 14 in the simulated-dye-spraying display mode.

Note, in items (c) and (d) of the timing chart of FIG. 6, a short time interval "t" corresponds to the time necessary to process the frame of red or green digital image-pixel-signals ($R_{ij}$, $G_{ij}$) in the color-balance alteration circuit 44. Namely, the writing of the processed red digital image-pixel-signals ($R_{ij}'$) in the R-signal frame memory 46R is delayed for the short time interval "t", and the writing of the processed green digital image-pixel-signals ($G_{ij}'$) in the G-signal frame memory 46G is also delayed for the short time interval "t".

Figure 7:
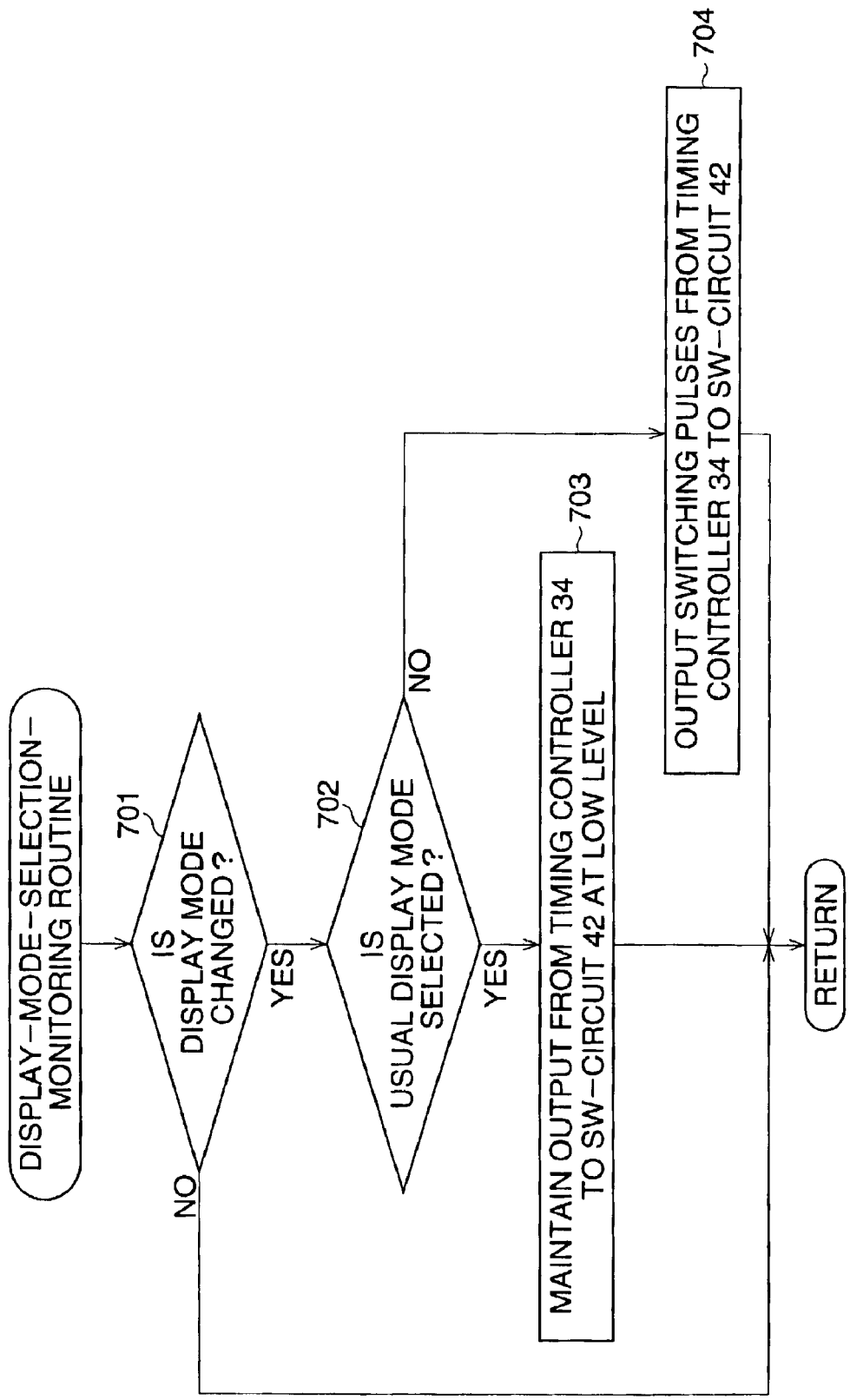
FIG. 7 is a flowchart of a display-mode-selection-monitoring routine executed in a system control circuit included in the first embodiment of the electronic endoscope system.

FIG. 7 shows a flowchart of a display-mode-selection-monitoring routine, which is formed as a time-interruption routine executed in the system control circuit 32 at regular suitable intervals of, for example, 20 ms. The execution of the routine is started after the power ON/OFF switch 56 is turned ON, and is repeated every 20 ms as long as the power ON/OFF switch 56 is turned ON.

At step 701, it is monitored whether either the usual display mode or the simulated-dye-spraying display mode has been changed to the other display mode by operating either the display mode selection switch 54 or the function key concerned on the keyboard 58. When the change of the display mode is not confirmed, the routine immediately ends. Although the routine is repeatedly executed every 20 ms, there is no progress until the change of the display mode is confirmed.

At step 701, when it is confirmed that the display mode has been changed, the control proceeds to step 702, in which it is determined whether the usual display mode has been selected. When the selection of the usual display mode is confirmed, the control proceeds to step 703, in which the output from the timing controller 34 to the switching-circuit 42 is maintained at the low level, as indicated by item (b) in the timing chart of FIG. 5, whereby the connection is established between the input terminal "IN" and the first output terminal "OUT1" in the switching-circuit 42.

At step 702, when the selection of the usual display mode is not confirmed, i.e. when it is confirmed that the simulated-dye-spraying display mode has been selected, the control proceeds from step 702 to step 704, in which the switching pulses are output from the timing controller 34 to the switching-circuit 42, as indicated by item (b) in the timing chart of FIG. 6, whereby the connection is established between the input terminal "IN" and the second output terminal "OUT2" in the switching-circuit 42 while only the frames of red and green digital image-pixel-signals ($R_{ij}$ and $G_{ij}$) are read from the frame memory 40.

Note, as stated above, whenever the power ON/OFF switch 56 is turned ON, the usual display mode is forcibly selected, and thus the connection is initially established between the input terminal "IN" and the first output terminal "OUT1" in the switching-circuit 42.

In the first embodiment, although the setting of "−50" is given to the second constant "k2", it is possible to optionally vary an absolute value of the second constant "k2" by operating the keyboard 58, and varying the absolute value of the second constant "k2" corresponds to using blue-dye solutions having different blue densities.

Figure 8:
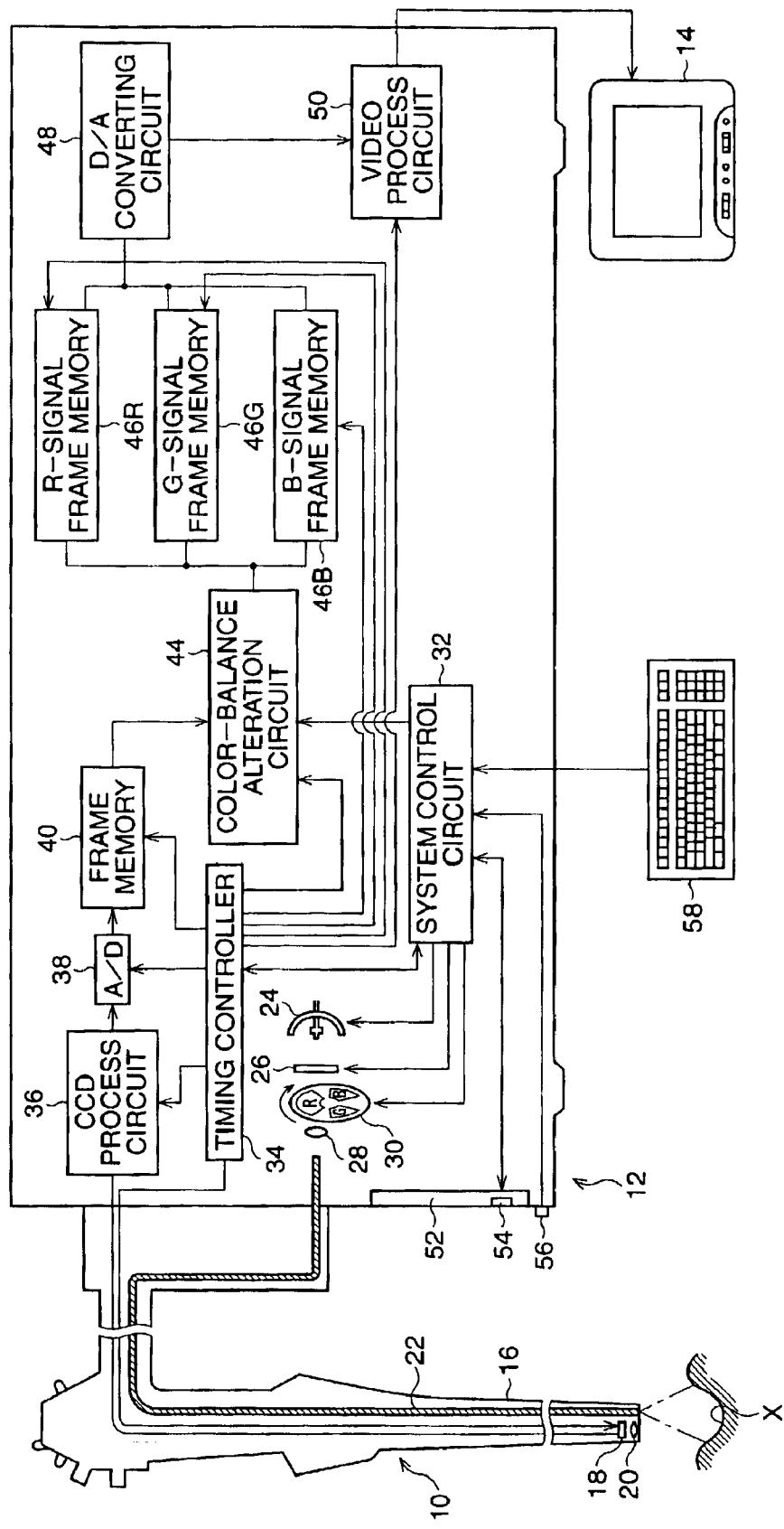
FIG. 8 is a schematic block diagram of a second embodiment of an electronic endoscope system according to the present invention.

Referring to FIG. 8, a second embodiment of an electronic endoscope system according to the present invention is shown as a block diagram. Note, in this drawing, the features similar to those of FIG. 1 are indicated by the same references.

As is apparent from FIG. 8, the second embodiment is substantially identical to the first embodiment except that the switching-circuit 42 is omitted from the image-signal processor in the image-signal processing unit 12. Thus, in the second embodiment, the frames of red, green, and blue image-pixel-signals ($R_{ij}$, $G_{ij}$, and $B_{ij}$) are cyclically and sequentially fed from the frame memory 40 to the color-balance alteration circuit 44, regardless of the selection of either the usual display mode or the simulated-dye-spraying display mode.

While the usual display mode is selected, the setting of "0" is forcibly given to the second constant "k2". Thus, during the selection of the usual display mode, the frames of red, green, and blue image-pixel-signals ($R_{ij}$, $G_{ij}$, and $B_{ij}$) can pass through the color-balance alteration circuit 44 without being subjected to any color-balance alteration process, due to the setting of "0" for the second constant "k2". Namely, the endoscope image is reproduced on the TV monitor 14 in the usual display mode.

Figure 9:
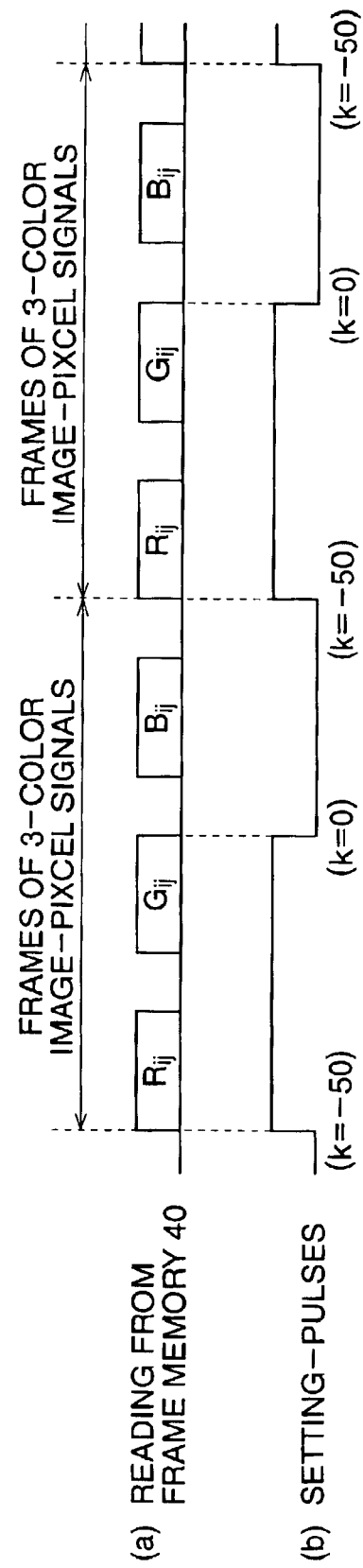
FIG. 9 is an operational timing chart for explaining an operation of the second embodiment of the electronic endoscope system in a simulated-dye-spraying display mode.

While the simulated-dye-spraying display mode is selected, the settings of "−50" and "0" are alternately given to the second constant "k2" in synchronization with the reading of the frames of red, green, and blue image-pixel-signals ($R_{ij}$, $G_{ij}$, and $B_{ij}$) from the frame memory 40, as shown in an operational timing chart of FIG. 9. Namely, while the three frames of red, green, and blue digital image-pixel-signals ($R_{ij}$, $G_{ij}$, and $B_{ij}$) are cyclically and sequentially read from the frame memory 40, as indicated by item (a) in the timing chart of FIG. 9, setting-pulses are output from the timing controller 34 to the system control circuit 32, as indicated by item (b) in the timing chart of FIG. 9.

In particular, as is apparent from the timing chart of FIG. 9, at a leading edge of each setting-pulse at which the reading of the frame of red digital image-pixel-signals ($R_{ij}$) from the frame memory 40 is started, the system control circuit 32 gives the setting of "−50" to the second constant "k2". At a trailing edge of each setting-pulse at which the reading of the frame of green digital image-pixel-signals ($G_{ij}$) from the frame memory 40 ends, the system control circuit 32 gives the setting of "0" to the second constant "k2". Thus, only the frames of red and green digital image-pixel-signals ($R_{ij}$ and $G_{ij}$) are subjected to the color-balance alteration process, due to the setting of "−50" to the second constant "k2", and the frame of blue digital image-pixel-signals is not subjected to any color-balance alteration process, due to the setting of "0" to the second constant "k2", whereby the endoscope image is reproduced on the TV monitor 14 in the simulated-dye-spraying display mode.

Figure 10:
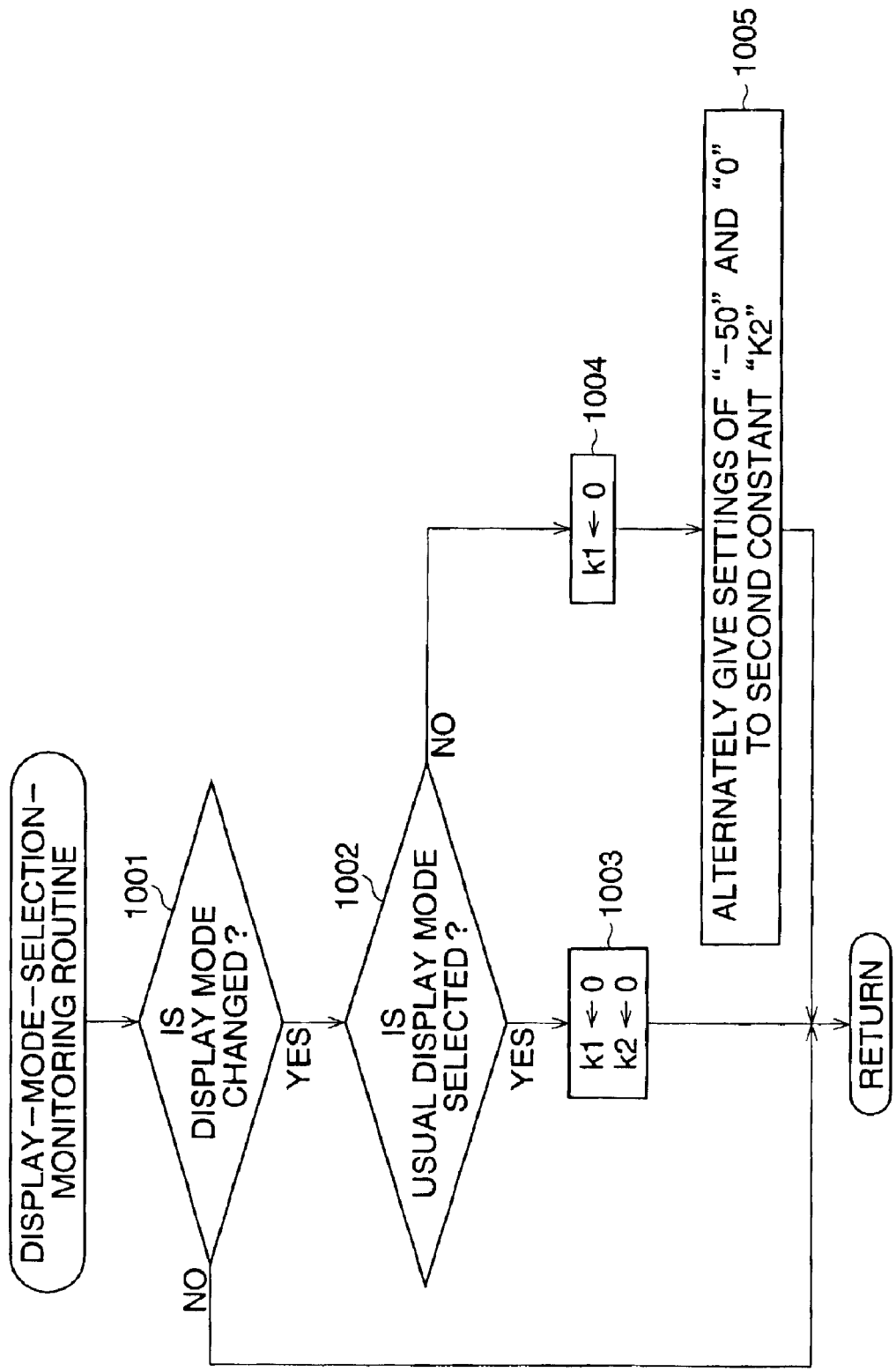
FIG. 10 is a flowchart of a display-mode-selection-monitoring routine executed in a system control circuit included in the second embodiment of the electronic endoscope system.

FIG. 10 shows a flowchart of a display-mode-selection-monitoring routine, which is executed in the system control circuit 32 of the second embodiment shown in FIG. 8. This routine is also formed as a time-interruption routine executed at regular suitable intervals of, for example, 20 ms. The execution of the routine is started after the power ON/OFF switch 56 is turned ON, and is repeated every 20 ms as long as the power ON/OFF switch 56 is turned ON.

At step 1001, it is monitored whether either the usual display mode or the simulated-dye-spraying display mode has been changed to the other display mode by operating either the display mode selection switch 54 or the function key concerned on the keyboard 58. When the change of the display mode is not confirmed, the routine immediately ends. Although the routine is repeatedly executed every 20 ms, there is no progress until the change of the display mode is confirmed.

At step 1001, when it is confirmed that the display mode has been changed, the control proceeds to step 1002, in which it is determined whether the usual display mode has been selected. When the selection of the usual display mode is confirmed, the control proceeds to step 1003, in which the settings of "0" is given to the first and second constants "k1" and "k2".

At step 1002, when the selection of the usual display mode is not confirmed, i.e. when it is confirmed that the simulated-dye-spraying display mode has been selected, the control proceeds from step 1002 to step 1004, in which the setting of "0" is given to the first constant "k1". Then, at step 1003, the settings of "−50" and "0" are alternately given to the second constant "k2" in accordance with the setting-pulses, as indicated by item (b) in the timing chart of FIG. 9, which are output from the timing controller 34 to the system control circuit 32.

Note, since the usual display mode is forcibly selected whenever the power ON/OFF switch 56 is turned ON, the setting of "0" for both the first and second constant "k1" and "k2" is automatically performed after the turn-ON of the power ON/OFF switch 56.

Figure 11:
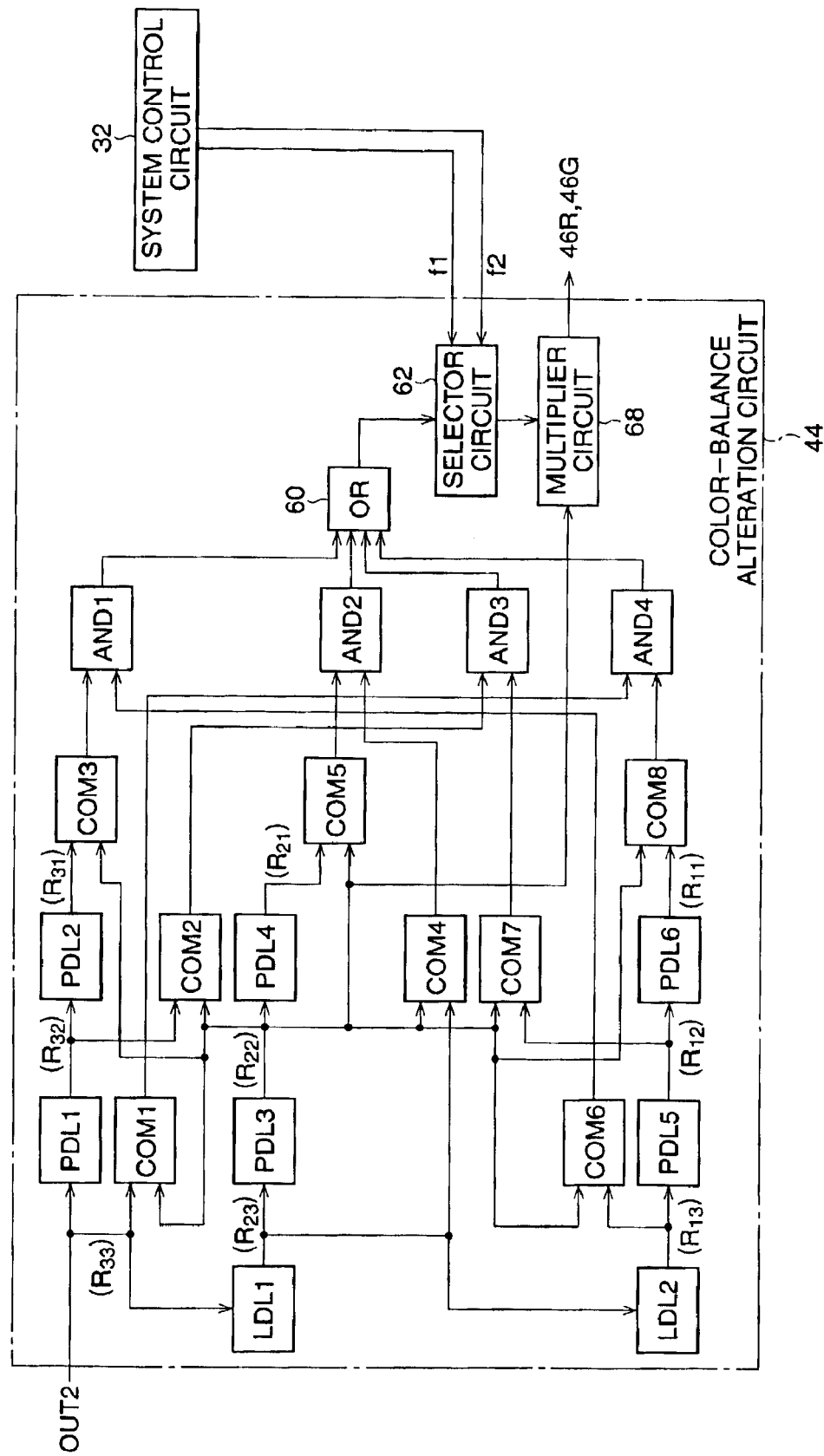
FIG. 11 is a schematic block diagram of a modification of the color-balance alteration circuit shown in FIG. 3.

FIG. 11 shows a modification of the color-balance alteration circuit 44. The modified color-balance alteration circuit 44 is substantially identical to that shown in FIG. 3, except that a multiplier circuit 68 is substituted for the adder circuit 64 and the clipping circuit 66.

In the modified color-balance alteration circuit 44, a first factor "f1" and a second factor "f2" are output from the system control circuit 32 to the selector circuit 62, and either the first factor "f1" or the second factor "f2" is selectively output from the selector circuit 62 to the multiplier circuit 68 in accordance with an output signal-level of the OR-gate circuit 60. Namely, when the low-level signal "0" is output from the OR-gate circuit 62 and input to the selector circuit 62, the first factor "f1" is output from the selector circuit 62. When the high-level signal "1" is output from the OR-gate circuit 62 and input to the selector circuit 62, the second factor "f2" is output from the selector circuit 62. A setting of "1" is always given to the first factor "f1", and a setting of less than one, for example, "0.5" is given to the second factor "f2".

Thus, when the area, from which the central pixel-signal ($R_{ij}$, $G_{ij}$) is derived, is regarded as a fine recess area, i.e. when the high-level signal "1" is output from the OR-gate circuit 60 and input to the selector circuit 62, the level value of the central pixel-signal ($R_{ij}$, $G_{ij}$) is multiplied by the second factor "f2", being "0.5", resulting in a decrease of the level value of the central pixel-signal ($R_{ij}$, $G_{ij}$). On the other hand, when the area, from which the central pixel-signal ($R_{ij}$, $G_{ij}$) is derived, cannot be regarded as a fine recess area, i.e. when the high-level signal "0" is input from the OR-gate circuit 60 to the selector circuit 62, the level value of the central pixel-signal ($R_{ij}$, $G_{ij}$) is multiplied by the first factor "f1", being "1", and thus the central pixel-signal ($R_{ij}$, $G_{ij}$) is output from the multiplier circuit 68 as it presently stands.

Accordingly, while the simulated dye-spraying display mode is selected, a color image-pixel on the TV monitor 14, represented by the color image-pixel-signals $R_{ij}$, $G_{ij}$, and $B_{ij}$, becomes bluish. Namely, a bluish endoscope image is observed on the TV monitor 14 as if an endoscope image, sensed by the CCD image sensor 18, were sprayed with a blue-solution.

When the modified color-balance alteration circuit 44 is used in the second embodiment (FIG. 8), a display-mode-selection-monitoring routine similar to that of FIG. 10 may be executed. Namely, when the usual display mode is selected, the setting of "1" is given to the first and second factors "f1" and "f2" (step 1003). Also, when the simulated-dye-spraying display mode is selected, the setting of "1" is given to the first factor "f1", and the setting of "0.5" and the setting of "1" are alternately given to the second factor "f2" in accordance with the setting-pulses, as indicated by item (b) in the timing chart of FIG. 9.

In short, at the leading edge of each setting-pulse at which the reading of the frame of red digital image-pixel-signals ($R_{ij}$) from the frame memory 40 is started, the system control circuit 32 gives the setting of "0.5" to the second factor "f2", and at the trailing edge of each setting-pulse at which the reading of the frame of green digital image-pixel-signals ($G_{ij}$) from the frame memory 40 ends, the system control circuit 32 gives the setting of "1" to the second factor "f2".

Note, it is possible to optionally vary a value of the second factor "f2" by operating the keyboard 58, and the varying of the value of the second factor "f2" corresponds to use of a blue-dye solution having a different blue density.

Figure 12:
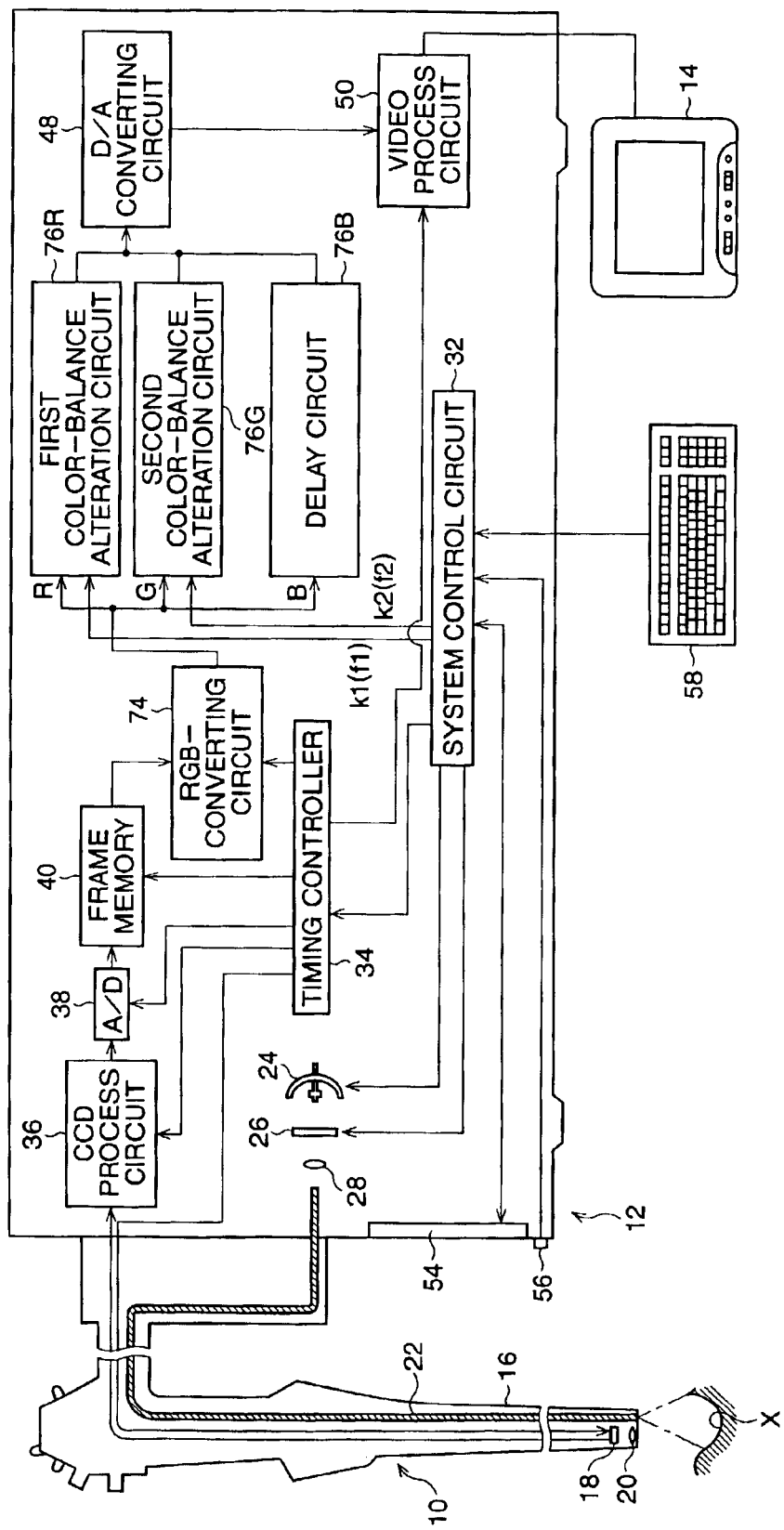
FIG. 12 is a schematic block diagram of a third embodiment of an electronic endoscope system according to the present invention.

Referring to FIG. 12, a third embodiment of an electronic endoscope system according to the present invention is shown as a block diagram. In this drawing, the features similar to those of FIG. 1 are indicated by the same references.

In the third embodiment, an on-chip color filter method (i.e., a simultaneous imaging method) is introduced to reproduce an endoscope image as a full color image on a TV monitor 14, instead of the RGB field sequential-type color imaging method, and a video scope 10 and an image-signal processing unit 12 are modified so as to conform to the on-chip color filter method.

In particular, a CCD image sensor 18 has a complementary color filter (not shown) provided on a light-receiving surface thereof. Also, a light source device, provided in the image-signal processing unit 12, is formed by a white light lamp 24, a diaphragm 26, and a condenser lens 28. Namely, the rotary color-filter 30 is eliminated from the light source device. Thus, white light is irradiated as an illuminating-light from a distal end face of an optical light guide 22. An illuminated object is focussed as an optical endoscope image on the light-receiving surface of the CCD image sensor 18 through the complementary color filter by an objective lens system 20, and the focussed endoscope image is converted into a frame of analog color image-pixel-signals due to the existence of the complementary color filter.

In the third embodiment, the image-signal processing unit 12 is also provided with a system control circuit 32 which controls the electronic endoscope system as a whole, and a timing controller 34 which outputs various series of clock pulses having given frequencies under the control of the system control circuit 32, to thereby operate sequentially and systematically an image-signal processor provided in the image-signal processing unit 12.

In the third embodiment, the image-signal processor, provided in the image-signal processing unit 12, includes a CCD process circuit 36, an analog-to-digital (A/D) converter 38, a frame memory 40, an RGB-converting circuit 74, a first color-balance alteration circuit 76R, a second color-balance alteration circuit 76G, a delay circuit 76B, a digital-to-analog (D/A) converting circuit 48, and a video-process circuit 50.

Similar to the first embodiment, when the connection between the video scope 10 and the image-signal processing unit 12 is established, the CCD image sensor 18 is connected to the timing controller 34 and the CCD process circuit 36. The timing controller 34 produces and outputs a series of reading clock pulses to the CCD image sensor 18, whereby the frame of analog complementary color image-pixel-signals is sequentially and successively read from the CCD image sensor 18. The read analog complementary color image-pixel-signals are fed to the CCD process circuit 36, in which the analog complementary color image-pixel-signals are subjected to various image-processings, such as gamma-correction, white-balance correction, profile-enhancing, noise-elimination, black-level-clamping and so on. For these various image-processings, the CCD process circuit 36 is operated in accordance with various series of clock pulses output from the timing controller 34.

Each of the processed analog complementary color image-pixel-signals is output from the CCD process circuit 36 to the A/D converter 38, in which the analog image-pixel-signal concerned is converted into a digital image-pixel-signal. The A/D converter 38 successively outputs digital complementary color image-pixel-signals, which are temporarily stored in the frame memory 40. The digital complementary color image-pixel-signals are successively read from the frame memory 40, and are then fed to the RGB-converting circuit 74, in which the digital complementary color image-pixel-signals are processed to thereby produce a red digital image-pixel-signal, a green digital image-pixel-signal, and a blue digital image-pixel-signal with the interpolation and the color conversion. The produced red, green, and blue digital image-pixel-signals R, G, and B are simultaneously output from the RGB-converting circuit 74 to the respective first and second color-balance alteration circuits 76R and 76G, and the delay circuit 76B.

The first and second color-balance alteration circuits 76R and 76G are substantially identical to each other, and both circuits (76R, 76G) may be the same as the color-balance alteration circuit 44 (FIG. 3) used in the first embodiment. Two frames of red and green digital image-pixel-signals ($R_{ij}$ and $G_{ij}$) are processed in the first and second color-balance alteration circuits 76R and 76G, and are then fed to the D/A converting circuit 48. On the other hand, a frame of blue image-pixel-signals ($B_{ij}$) fed to the D/A converting circuit 48 through the delay circuit 78B. Namely, the delay circuit 78B delays the outputting of the blue image-pixel-signal ($B_{ij}$) by a time necessary to process the red and green digital image-signals ($R_{ij}$ and $G_{ij}$) in the first and second color-balance alteration circuits 76R and 76G. In short, the processed red and green digital image-signals ($R_{ij}$ and $G_{ij}$) and the delayed blue image-pixel-signal ($B_{ij}$) are simultaneously input to the D/A converting circuit 48.

The red, green, and blue digital image-pixel-signals ($R_{ij}$, $G_{ij}$ and $B_{ij}$ are simultaneously converted into red, green, and blue analog signals by the D/A converting circuit 48, and the red, green, and blue analog image signals are output to the video process circuit 50. On the other hand, the timing controller 34 produces a composite synchronizing signal, and the composite synchronizing signal is output from the timing controller 34 to the video process circuit 50. Thus, similar to the first embodiment, the video process circuit 50 produces a component type video signal based on the red, green, and blue analog image signals output from the D/A converting circuit 48, and the synchronizing signal output from the timing controller 34. Accordingly, an endoscope image, sensed by the CCD image sensor 18, is reproduced as a full color motion picture on the TV monitor 14.

In both the first and second color-balance alteration circuits 76R and 76G, the setting of "0" is given the first constant "k1" and the second constant "k2" while a usual display mode is selected. Thus, the respective red and green digital image-signals ($R_{ij}$ and $G_{ij}$) pass through the first and second color-balance alteration circuits 76R and 76G without being subjected to any color-balance alteration process. Accordingly, during the selection of the usual display mode, the reproduction of the endoscope image on the TV monitor 14 is performed with a given proper color balance.

While a simulated-dye-spraying display mode is selected, the setting of "0" is given the first constant "k1" and the setting of, for example, "−50" is given to the second constant "k2" in both the first and second color-balance alteration circuits 76R and 76G. Thus, when the red and green color image-pixel-signals $R_{ij}$ and $G_{ij}$, are derived from a fine recess area on a mucous membrane surface of an internal organ, the respective signal-level values of the red and green image-pixel-signals $R_{ij}$ and $G_{ij}$ are decreased by the absolute value of the second constant "k2", but the signal-level value of the blue image-pixel-signal $B_{ij}$ cannot be deceased. Accordingly, during the selection of the simulated dye-spraying display mode, the reproduction of the endoscope image on the TV monitor 14 is performed as if the endoscope image, sensed by the CCD image sensor 18, were sprayed with a blue-solution.

In the third embodiment, each of the first and second color-balance alteration circuits 76R and 76G may comprise the modified color-balance alteration circuit 44 as shown in FIG. 11. In this case, of course, in the usual display mode, the setting of "1" is given to the first and second factors "f1" and "f2", and, in the simulated-dye-spraying display mode, the settings of "1" and "0.5" are given the first and second factors "f1" and "f2".

Figure 13:
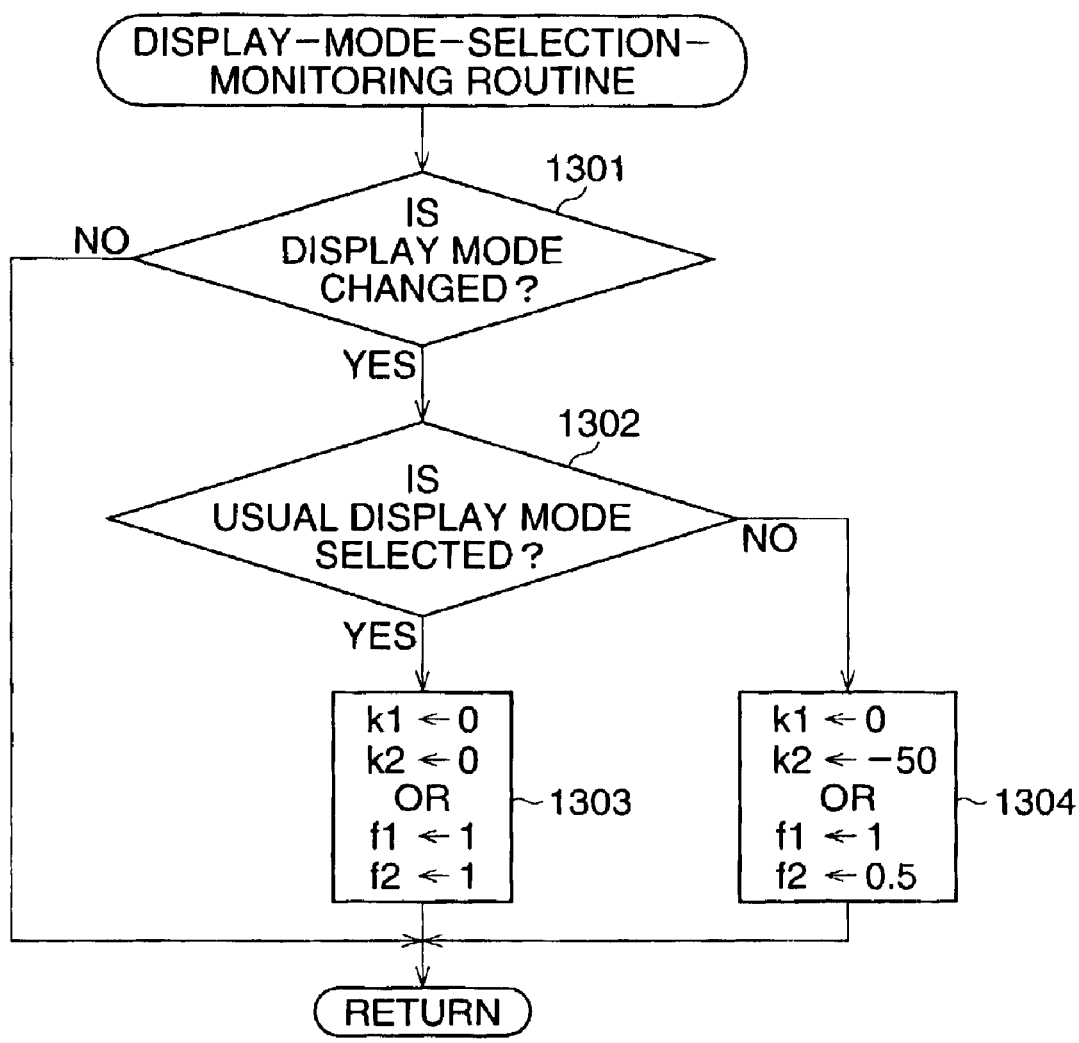
FIG. 13 is a flowchart of a display-mode-selection-monitoring routine executed in a system control circuit included in the third embodiment of the electronic endoscope system.

FIG. 13 shows a flowchart of a display-mode-selection-monitoring routine, which is executed in the system control circuit 32 of the third embodiment shown in FIG. 12. This routine is also formed as a time-interruption routine executed at regular suitable intervals of, for example, 20 ms. The execution of the routine is started after the power ON/OFF switch 56 is turned ON, and is repeated every 20 ms as long as the power ON/OFF switch 56 is turned ON.

At step 1301, it is monitored whether either the usual display mode or the simulated-dye-spraying display mode has been changed to the other display mode by operating either the display mode selection switch 54 or the function key concerned on the keyboard 58. When the change of the display mode is not confirmed, the routine immediately ends. Although the routine is repeatedly executed every 20 ms, there in no progress until the change of the display mode is confirmed.

At step 1301, when it is confirmed that the display mode has been changed, the control proceeds to step 1302, in which it is determined whether the usual display mode has been selected. When the selection of the usual display mode is confirmed, the control proceeds to step 1303, in which the setting of "0" is given to the first and second constants "k1" and "k2" when using the color-balance alteration 44 shown in FIG. 3 or in which the setting of "1" is given to the first and second factors "f1" and "f2" when using the modified color-balance alteration 44 shown in FIG. 11.

At step 1302, when the selection of the usual display mode is not confirmed, i.e. when it is confirmed that the simulated-dye-spraying display mode has been selected, the control proceeds from step 1302 to step 1304, in which the settings of "0" and "−50" are given to the first and second constants "k1" and "k2" when using the color-balance alteration 44 shown in FIG. 3, or the settings of "1" and "0.5" are given to the first and second factors "f1" and "f2" when using the modified color-balance alteration 44 shown in FIG. 11.

Finally, it will be understood by those skilled in the art that the foregoing descriptions are of preferred embodiments of the systems, and that various changes and modifications may be made to the present invention without departing from the spirit and scope thereof.

The present disclosure relates to subject matters contained in Japanese Patent Application No. 2001-324697 (filed on Oct. 23, 2001), which is expressly incorporated herein, by reference, in its entirety.

What is claimed is:

1. An electronic endoscope system including a video scope having a solid-state image sensor that successively produces a frame of color image-pixel-signals composed of at least two frames of different monochromatic image-pixel-signals, which comprises a color-balance alteration system including:

an extraction system that successively extracts a set of monochromatic image-pixel-signals from a frame of monochromatic image-pixel-signals, the set of monochromatic image-pixel-signals being composed of a central monochromatic image-pixel-signal, and neighbouring monochromatic image-pixel-signals surrounding said central monochromatic image-pixel-signal;

a selection system that selects all sets of three monochromatic image-pixel-signals from said set of monochromatic image-pixel-signals, each set of three monochromatic image-pixel-signals being composed of said central monochromatic image-pixel-signal, and two neighbouring monochromatic image-pixel-signals aligned with each other such that said central monochromatic image-pixel-signal lies therebetween;

a determination system that determines whether a signal level of said central monochromatic image-pixel-signal is smaller than signal levels of said two neighbouring monochromatic image-pixel-signals with respect to all said sets of three monochromatic image-pixel-signals; and a decrease system that decreases the signal level of said central monochromatic image-pixel-signal when it is determined by said determination system that the signal level of said central monochromatic image-pixel-signal is smaller than both the signal levels of said two neighbouring monochromatic image-pixel-signals in at least one of the sets of three monochromatic image-pixel-signals.

2. An electronic endoscope system as set forth in claim 1, wherein said decrease system comprises a subtraction system that subtracts a predetermined level value from the signal level of said central monochromatic image-pixel-signal.

3. An electronic endoscope system as set forth in claim 1, wherein said decrease system comprises a multiplier system that multiplies the signal level of said central monochromatic image-pixel-signal by a predetermined factor less than one.

4. An electronic endoscope system as set forth in claim 1, further comprising:
- a first video signal production system that produces a first type of video signal based on the frame of color image-pixel-signals;
- a second video signal production system that produces a second type of video signal based on the frame of color image-pixel-signals composed of the frame of monochromatic image-pixel-signals processed by said color-balance alteration system; and
- a monitor system that selectively displays a first image and a second image based on said first and second types of video signals, respectively.

5. An electronic endoscope system as set forth in claim 4, further comprising:
- a display-mode selection system that selects either a first display mode or a second display mode; and
- a display control system that displays said first image on said monitor system based on said first type of video signal when the first display mode is selected by said display-mode selection system, and that displays said second image on said monitor system based on said second type of video signal when the second display mode is selected by said display-mode selection system.

6. An electronic endoscope system as set forth in claim 5, further comprising:
- a disablement system that disables said color-balance alteration system when the first display mode is selected by said display-mode selection system; and
- an enablement system that enables said color-balance alteration system when the second display mode is selected by said display-mode selection system.

* * * * *